United States Patent
Kreck

(10) Patent No.: US 8,308,787 B2
(45) Date of Patent: Nov. 13, 2012

(54) RAPID COOLING OF BODY AND/OR BRAIN BY IRRIGATING WITH A COOLING LIQUID

(75) Inventor: Thomas Kreck, San Francisco, CA (US)

(73) Assignee: NeuroSave, Inc., San Francisco, CA (US)

( * ) Notice: Subject to any disclaimer, the term of this patent is extended or adjusted under 35 U.S.C. 154(b) by 283 days.

(21) Appl. No.: 12/842,860

(22) Filed: Jul. 23, 2010

(65) Prior Publication Data

US 2010/0324635 A1    Dec. 23, 2010

Related U.S. Application Data

(63) Continuation-in-part of application No. PCT/US2009/031924, filed on Jan. 24, 2009.

(60) Provisional application No. 61/023,706, filed on Jan. 25, 2008.

(51) Int. Cl.
  *A61F 7/00* (2006.01)
(52) U.S. Cl. ............... 607/105; 607/104; 607/113
(58) Field of Classification Search .......... 607/104, 607/105, 113
  See application file for complete search history.

(56) References Cited

U.S. PATENT DOCUMENTS

| | | |
|---|---|---|
| 3,776,241 A | 12/1973 | Magilton et al. |
| 3,897,790 A | 8/1975 | Magilton et al. |
| 4,060,079 A | 11/1977 | Reinhold, Jr. |
| 4,111,209 A | 9/1978 | Wolvek et al. |
| 4,666,425 A | 5/1987 | Fleming |
| 4,750,493 A | 6/1988 | Brader |
| 4,920,963 A | 5/1990 | Brader |
| 5,261,399 A | 11/1993 | Klatz et al. |
| 5,531,776 A | 7/1996 | Ward et al. |
| 5,716,386 A | 2/1998 | Ward et al. |
| 5,755,756 A | 5/1998 | Freedman, Jr. et al. |
| 5,865,176 A * | 2/1999 | O'Neil ............... 128/207.15 |
| 5,913,885 A | 6/1999 | Klatz et al. |
| 5,916,242 A | 6/1999 | Schwartz |

(Continued)

FOREIGN PATENT DOCUMENTS

EP    1 935 382    6/2008

(Continued)

OTHER PUBLICATIONS

Brown et al., "Profound Selective Cerebral Hypothermia in Dogs by Naso-Oral Perfusion and Head Immersion," *Surgical Forum* 15:413-415, 1964.

(Continued)

*Primary Examiner* — Roy Gibson
(74) *Attorney, Agent, or Firm* — Fulbright & Jaworski L.L.P.

(57) ABSTRACT

Methods and devices are disclosed for providing therapeutic hypothermia using irrigation of the aerodigestive tract with cooled liquids. The disclosed method provides much more rapid therapeutic cooling to lower temperatures than could previously be achieved, thereby improving clinical outcomes. Novel cooling liquids and cooling devices are disclosed for carrying out the method. An external turbulent flow of cooling liquid may also be applied to the exterior of the head to further promote heat exchange. Multiple embodiments of devices are disclosed for performing rapid induction and maintenance of therapeutic hypothermia either in a hospital setting or in the field so that hypothermic treatment can be quickly instituted before significant tissue damage occurs. Methods are also disclosed for targeting brain cooling by irrigating the upper airway/aerodigestive tract, and more generalized cooling by irrigating the esophagus and/or stomach.

27 Claims, 11 Drawing Sheets

U.S. PATENT DOCUMENTS

| | | | |
|---|---|---|---|
| 5,927,273 | A | 7/1999 | Federowicz et al. |
| 6,149,624 | A | 11/2000 | McShane |
| 6,511,502 | B2 | 1/2003 | Fletcher |
| 6,599,312 | B2 | 7/2003 | Dobak, III |
| 6,620,189 | B1 | 9/2003 | Bloom et al. |
| 6,623,098 | B2 | 9/2003 | Davis |
| 6,694,977 | B1 | 2/2004 | Federowicz et al. |
| 6,719,779 | B2 | 4/2004 | Daoud |
| 6,736,790 | B2 | 5/2004 | Barbut et al. |
| 6,849,072 | B2 | 2/2005 | Lee et al. |
| 6,962,601 | B2 | 11/2005 | Becker et al. |
| 7,052,509 | B2 | 5/2006 | Lennox et al. |
| 7,144,418 | B1 | 12/2006 | Lennox |
| 7,156,867 | B2 | 1/2007 | Lennox |
| 7,189,253 | B2 | 3/2007 | Lunderqvist et al. |
| 7,189,254 | B2 | 3/2007 | Magers |
| 7,666,215 | B2 | 2/2010 | Callister et al. |
| 7,758,623 | B2 | 7/2010 | Dzeng et al. |
| 7,837,722 | B2 | 11/2010 | Barbut et al. |
| 7,892,271 | B2 | 2/2011 | Schock et al. |
| 2002/0120317 | A1 | 8/2002 | Fletcher |
| 2003/0130651 | A1 | 7/2003 | Lennox |
| 2004/0267339 | A1 | 12/2004 | Yon et al. |
| 2006/0069418 | A1 | 3/2006 | Schock et al. |
| 2007/0123813 | A1 | 5/2007 | Barbut et al. |
| 2007/0240722 | A1 | 10/2007 | Kessler |
| 2008/0086186 | A1 | 4/2008 | Takeda et al. |
| 2009/0177258 | A1 | 7/2009 | Takeda et al. |
| 2010/0198319 | A1 | 8/2010 | Arad |

FOREIGN PATENT DOCUMENTS

| | | |
|---|---|---|
| JP | 10192331 | 7/1998 |
| WO | WO 99/05996 | 2/1999 |
| WO | WO 01/39692 | 6/2001 |
| WO | WO 2006/124702 | 11/2006 |
| WO | WO 2009/094601 | 7/2009 |

OTHER PUBLICATIONS

White et al., "Rapid Selective Brain-Cooling Using Head Immersion and Naso-Oral Perfusion in Dogs," *Resuscitation* 10:189-191, 1983.

International Search Report from International Application No. PCT/US2009/031924 dated Aug. 31, 2009.

Written Opinion of the International Search Report from International Application No. PCT/US2009/031924 dated Aug. 31, 2009.

* cited by examiner

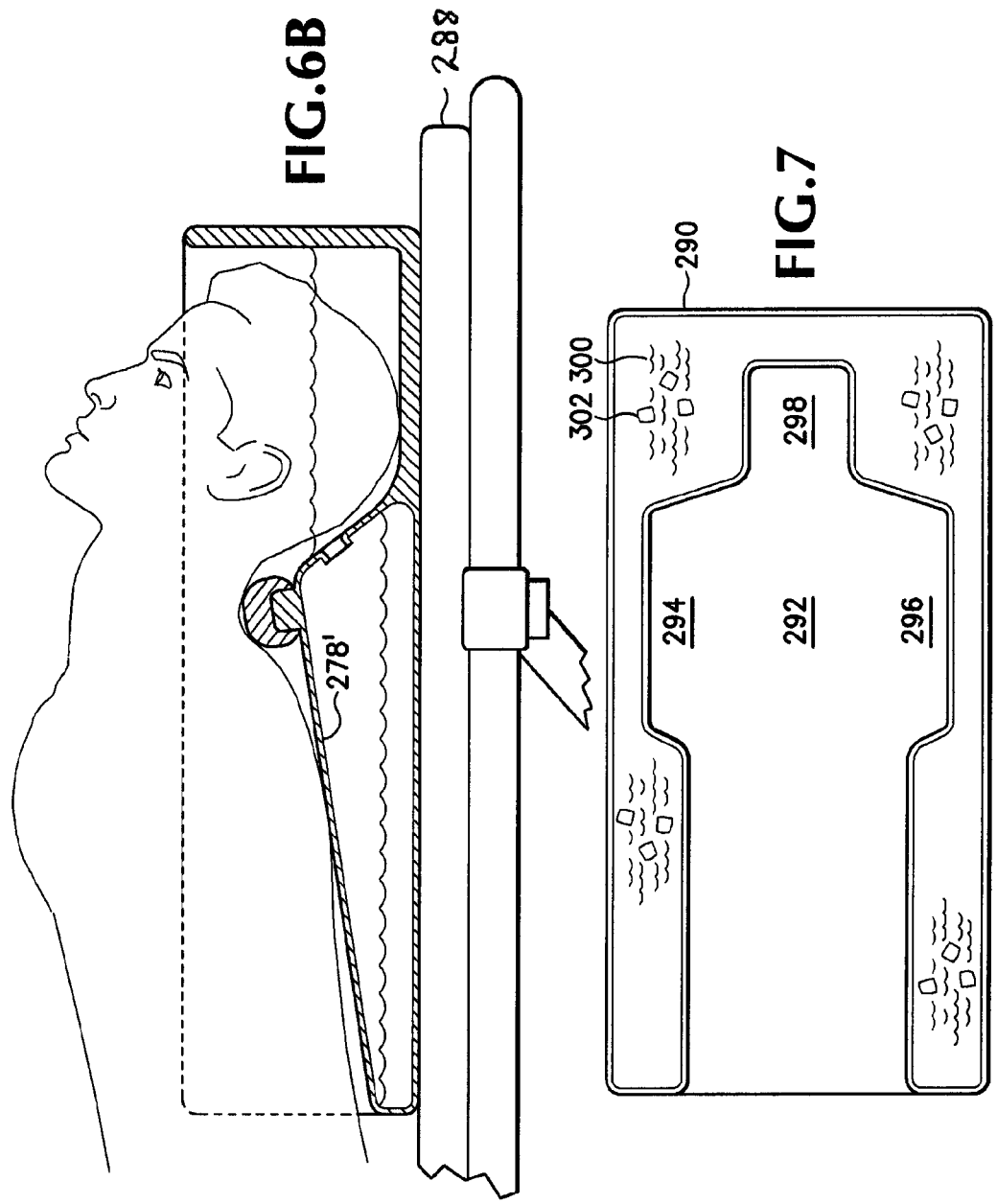

US 8,308,787 B2

RAPID COOLING OF BODY AND/OR BRAIN BY IRRIGATING WITH A COOLING LIQUID

RELATED APPLICATION

This application is a continuation-in-part of PCT Patent Application No. PCT/US2009/031924, filed on Jan. 24, 2009, which in turn claims the benefit of U.S. Provisional Application No. 61/023,706, filed Jan. 25, 2008. Each of these applications is incorporated herein by reference in its entirety.

FIELD

A device and method are disclosed for inducing rapid cooling of the brain and/or body in a subject.

BACKGROUND

Permanent damage to the brain is a common sequelae of stroke, trauma and cardiac arrest. Each year in the United States, over 350,000 people experience an out-of-hospital cardiac arrest, and only 6.4% survive until hospital discharge without significant neurological damage. Cardiac arrest is the leading cause of death in the United States, with a direct medical cost of $2 billion per year. Stroke is the third leading cause of death and the leading cause of disability, with the cost of treatment, supportive care and lost productivity estimated at $43 billion per year. There are more than 1.5 million new head injuries in United States each year with an estimated annual cost of $53 billion. About 5.3 million people in the United States (2% of the population) are living with a permanent disability from traumatic brain injury. In spite of the tremendous financial cost and personal suffering caused by these conditions, currently available techniques to reverse cerebral damage have been generally ineffective.

There are well documented cases of incidentally preserved neurological function in drowning victims who have had prolonged cardiac arrest in cold water. Hypothermia can substantially reduce deterioration in hypoxic or anoxic neurological, myocardial or other tissue by slowing some of the thermodynamic tendency toward tissue death and by protecting against reperfusion injury. Tissue cooling can also reduce brain edema that raises intracranial pressure and reduces perfusion of already damaged brain tissue, or reduce swelling of the spinal cord that accompanies traumatic injury. Many other types of inflammation can also be reduced by cooling of affected tissue.

Animal studies have found significantly greater neurological function after cerebral anoxia if the brain is cooled; however human studies have not consistently found this benefit. The reasons for this difference are not well understood, but it is believed that the prolonged time needed to cool the brain using existing clinical methods is partially responsible for a lack of definitive benefits in humans. The depth of cooling may also be a therapeutically limiting factor.

Cerebral hypothermia treatment has previously employed cooling of the entire body to cool the brain. Total body cooling requires cooling of a mass much larger than the head that inherently slows the rate of brain cooling. For example, passive total body cooling by applying cold liquid or a cooling blanket to the skin induces hypothermia, but this approach is slow because of the low surface-to-volume ratio of the skin to the body. In addition, a therapeutically optimal body and brain temperature is often not achieved using these methods. Total body cooling also subjects other organ systems to the same or greater degree of cooling as the brain, risking unwanted systemic effects or damage.

Active total body cooling involves an intervention to more quickly cool the blood or internal body cavities. Such interventions often require highly skilled medical teams to implement them, and initiation of therapy may be significantly delayed due to the invasiveness and complexity of the treatment. Various methods of actively infusing cold liquids into the body have been described but these methods usually require cooling of the entire body in order to effect cooling of the brain. U.S. Pat. No. 5,927,273 discloses a cardiopulmonary resuscitation method in which gas in the lungs is replaced with a cooled oxygen-carrying liquid. U.S. Pat. No. 6,962,601 discloses phase-change perfluorocarbon particulate slurries that can be used to induce hypothermia by administering them internally or circulating them through a cooling cap or blanket.

Localized cooling of various structures in the head has been described but rates of cooling are slow and the desired level of cooling is often not achieved. Devices for enclosing the head in a helmet or shroud that externally circulates cooling fluid around the scalp are shown in U.S. Pat. Nos. 4,920,963; 5,755,756; and 7,052,509. U.S. Patent Publication No. 2007/0123813 discloses a method of cerebral and systemic cooling in which a nebulized liquid is delivered as a mist or spray to the nasal and/or oral cavities of a subject. A similar method is also disclosed in Brown et al., Surgical Forum 15:413-415, 1964, in which a dog's head was immersed in circulating ice water, and large bore catheters were inserted into the nostrils of an animal to perfuse the nasopharynx with ice water at a rate of 1.1 to 1.6 L/min An even more invasive localized hypothermia technique is illustrated in U.S. Pat. No. 7,156,867, which discloses a head-cooling cap and a brain-cooling probe for insertion into the lateral ventricle of the brain. Cooling liquid is infused through the probe into the ventricles of the brain to circulate cooling fluid and cool the brain.

U.S. Pat. No. 7,189,253 introduces cooled liquid through a catheter that is advanced through the nostril of a subject with the tip placed at the level of the back of the tongue. A balloon carried by the catheter is expanded with cold liquid to fill the nasal cavity without allowing the cool liquid to contact the walls of the nasal cavity or the vascular nasal mucosa.

None of these techniques is known to provide the rapid cerebral hypothermia that achieves desired tissue protection, for example against permanent neurological damage following brain insults such as cardiogenic shock, stroke or direct traumatic damage to the brain. The need for an improved device of this nature has been highlighted by recent efforts in the medical community to routinely provide head or body cooling to patients who have had a myocardial infarction, or are undergoing heart surgery, to avoid permanent brain injury. Such cooling methods range from total body immersion in cold liquid to lowering the thermostat in the hospital rooms of patients. However, such interventions have been largely unsuccessful, and many of them have required sophisticated devices and surgical interventions that have limited use of induced hypothermia outside of a hospital setting. There is a need for therapeutic hypothermia techniques that can selectively and rapidly cool the brain or the entire body, and for techniques that are suitable for rapid application outside a hospital under emergency conditions. There is also a need for techniques that can provide for deeper levels of hypothermia in the brain while keeping the body relatively warmer.

SUMMARY

The slow rate of cooling and delays in initial of treatment in prior therapeutic hypothermia devices and methods have been important reasons that hypothermic induction has not been more effective in preserving tissue function (such as neurological function) following hypoxia, myocardial function following myocardial infarction, or other types of function following inflammation or injury in clinical trials. These problems have been addressed herein by providing a system that permits much more rapid and/or deeper therapeutic hypothermia. In certain embodiments of the method, the cooling can be targeted to the brain (for example to preserve neurological function following a stroke, brain injury, myocardial infarction or episode of cardiac arrest) or more generally to the entire body (to control generalized inflammation or injury to non-brain structures such as the spinal cord or myocardium).

The improved system for inducing rapid hypothermia takes advantage of the inventor's recognition that the aerodigestive tract is capable of accommodating a much larger flow of cooling liquid than had previously been appreciated, and that a continuous flow of a high volume of liquid along the irregular surface of the tract provides unexpectedly rapid cooling to lower temperatures than were previously achievable in such short periods of time. In addition, the inventor recognizes the unexpected benefit of lengthening the region of the aerodigestive tract with regard to heat transfer and cooling the brain. By lengthening the regions of the aerodigestive tract that is cooled, and thereby increasing the residence time of the blood in the cooling zone, the inventor has increased the depth of cooling possible and the rate at which brain cooling can be achieved. This rapid cooling permits the method to be used more effectively in urgent situations so that effective cooling can be induced prior to completion of irreversible tissue damage. Following induction, the method is also capable of effectively maintaining cooling for sustained periods of time to provide maximal therapeutic benefit. Variations of the method can achieve targeted or selective cooling of the brain, or less selective cooling of both the brain and the body, as required by clinical conditions.

In certain disclosed embodiments, organ hypothermia is induced by introducing a high volume flow of non-nebulized cold, biologically compatible irrigation liquid into the aerodigestive tract but not the lungs of the subject so that the cold irrigation liquid substantially fills and directly contacts the walls of the aerodigestive tract to achieve rapid and effective heat exchange over the large and irregular surface of the tract that the liquid contacts. The cold irrigation liquid is maintained at a temperature of $-30°$ C. to $20°$ C., and is introduced into the length of aerodigestive tract. The liquid is allowed to flow in a coherent large volume mass through the aerodigestive tract and along the exposed irregular surface of the aerodigestive tract. In some embodiments, a turbulent flow of liquid is also directed externally against the head of the subject (such as the face and/or scalp) to further accelerate cooling. The head of the subject may be at least partially immersed in cold liquid that is agitated to apply the turbulent flow, and/or a flow of the cold liquid is directed toward the head of the subject from a liquid flow tube even when the head is not immersed in the cool liquid.

In one embodiment of the method, the irrigation liquid is introduced into the aerodigestive tract by placing catheters in the aerodigestive tract and flowing liquid through the catheters into the aerodigestive tract. The catheters in some examples are placed in the aerodigestive tract to introduce the liquid only above the level of the trachea and esophagus to achieve selective targeted cooling of the brain by primarily cooling the structures near the brain and in contact with blood vessels that supply blood to the brain.

In other examples, the catheters are placed to introduce the liquid into the esophagus and/or stomach to achieve non-selective organ cooling by bringing the liquid into contact with the insulated structures of the mediastinum through which venous blood returns to the heart. The insulated, small, anatomic chamber provided by the mediastinum permits excellent heat exchange with the circulating blood to achieve the desired rapid non-brain specific cooling effect. In addition to the placement of catheters in the esophagus and stomach, one or more catheters can also be placed to introduce the flow of liquid into the upper aerodigestive tract structures above the level of the esophagus to provide additional or maximal cooling. For example, the catheters are placed with their introduction ports or tips in the nasal cavity, oral cavity, and/or hypopharynx (and preferably all three). In other embodiments, the catheters have multiple lumens and/or multiple ports to introduce the cooling liquid at multiple points along the length of the catheters to increase the flows outside of the catheter that have been found to be effective in the rapid protective induction of therapeutic hypothermia.

The subject can also be intubated with an endotracheal tube having a cuff on the tube so that the cuff can be inflated to inhibit entry of the irrigation liquid into the lungs. An additional cuffed tube can be placed above the larynx to provide further inhibition of fluid entry into the lung. In addition, a tube with an inflatable balloon can be placed in the esophagus and the cuff inflated to substantially inhibit flow of liquid out of the upper airway into the lower esophagus and stomach. Isolating the gastrointestinal tract (including the esophagus) from the flow of cold liquid in the upper airway helps direct the cooling effect to the upper airway and the structures (including blood vessels) that are in heat transferring proximity with the cold liquid.

To help achieve and maintain rapid and effective cooling of the desired anatomic structures, it is useful to provide a sufficient reservoir of pre-cooled liquid for introduction internally into the aerodigestive tract and/or externally against the head. In view of the large volumes of cooling liquid that are circulated to induce rapid hypothermia and maintain it, an external reservoir of irrigation liquid is provided that supplies a sufficient volume of cool liquid at the selected flow rate. In some embodiments, the reservoir is also a container in which the head is completely or partially immersed. Alternatively the reservoir partially or completely surrounds a receptacle in which the head is placed, and the receptacle collects cooling liquid that flows out of the mouth and/or nose after it has circulated within the aerodigestive tract outside of the irrigation catheters. In other embodiments, the reservoir is placed in a back support that also contacts the back and optionally cools the body and structures of the back, such as the spinal cord. These and other embodiments can be incorporated into devices that can be attached to or will roll in tandem with a stretcher so that the hypothermia therapy can be administered to a patient in transit.

The liquid that is introduced into the aerodigestive tract leaves the aerodigestive tract by flowing out of the mouth and/or nose of the subject to return to the external reservoir. The return of the liquid can be passive, and not contained in a suction tube, so that the cool return liquid flows along the length of at least the upper airway or along the entire aerodigestive tract to intimately contact the entire irregular surface of that tract. In particular embodiments, the aerodigestive tract other than the lungs is substantially filled with the cooling liquid. Passive return of the liquid also helps avoid traumatic damage to the aerodigestive tract that could occur if a return lumen is occluded in a system that requires flow through such a circuit for removal. Liquid that flows out of the mouth and nose of the subject can return passively to the reservoir to be cooled, or circulated externally of the reservoir for cooling. In particular embodiments, the external reservoir is a container in which at least part of the head is contained, or over which the head is positioned, to collect the liquid that flows out of the mouth and/or nose of the subject by gravity-assisted flow of the liquid.

In particular embodiments of the method, the liquid reservoir is a neck support on which the neck of the subject is positioned with the neck tilted backwards (extended) to help protect the airway of the subject and promote the flow of liquids through the aerodigestive tract (and not the lungs). In embodiments in which the neck is extended, the head may be tilted back into a container of cool liquid to partially or substantially completely immerse the head in the cold liquid. Alternatively, the liquid reservoir is a back and neck support that helps stabilize the spine (for example in cases of possible spinal injury). The support itself may be hollow and contain the reservoir of cold liquid, or the support may be a body supporting platform suspended over a tub of cold water, for example a tub that is large enough to receive the body that is suspended above it and in which ice or other cold items are placed to provide the large supply of cooling liquid. In particular examples, the reservoir has 1-50 liters of cool liquid in it, or liquid to be cooled. The volume of cool liquid in the reservoir can vary depending on the clinical circumstances. For example, smaller volumes (1-20 L) are preferred outside of an inpatient setting (for example in an ambulance), but larger volumes (greater than 20, 30 or even 40 L) can be used for inpatient settings.

This specification also discloses multiple devices for carrying out the methods of inducing organ cooling in a subject. In one example, a head receptacle is adapted for receiving and maintaining a head of the subject at least partially immersed in cool liquid, and a neck support for supporting the neck of the subject with the head of the subject tilted backwards into the liquid container. The container can include a liquid reservoir of cold cooling liquid outside of the receptacle, or the receptacle itself can serve as the reservoir. The device further includes an outflow port for delivering cold liquid from the reservoir, and one or more outflow lines (such as catheters) are connected to the outflow port for placement in the aerodigestive tract of the subject. One or more pumps withdraw liquid from the reservoir to move it through the catheter and into the aerodigestive tract. In particular examples, the one or more pumps are capable of delivering a total of 0.5-50 L/min of cooling liquid to the aerodigestive tract of the subject. Flow rates in the higher range can increase the diameter of the compliant regions of the upper aerodigestive tract, such as the hypopharynx and esophagus, which can further improve heat transfer by increasing the surface area being cooled.

In one embodiment of the device, the liquid reservoir is a compartment that at least partially abuts the head receptacle, and a drain communicates between the head receptacle and the liquid reservoir to return liquid from the head receptacle to the liquid reservoir. The liquid reservoir may be an at least partially hollow backboard for supporting a back of a subject, and the backboard that contains the cooling liquid can be thermally conductive so that cool liquid within the backboard cools the back of a subject placed on the board. The backboard may include a top, body-supporting surface and an inclined neck tilt inducing surface that inclines into the head receptacle to support the body above the head receptacle. The top surface of the backboard may incline upwardly to elevate the thorax relative to the feet, and then downwardly to provide a downwardly sloping surface on which the head rests with the neck extended. The top surface of the backboard may further include a neck support that is placed at the level of the cervical spine of the subject. The neck support may be adjustable in height and/or padded.

One advantage of the disclosed method and device is that it is suitable for use outside of or in transit to the hospital, for example in an ambulance or on a stretcher that is being moved. For example, a wheeled stretcher has a body support surface on which a back board is placed, a neck support board that inclines from the back support board into a reservoir for liquid, and a head support member carried by the neck support board. The position of the head support member is adjustable along the neck support member to adjust the head at a desired height (or depth) in the reservoir. In some embodiments, a wheeled support is provided beneath the reservoir so that the reservoir can be wheeled in tandem with the stretcher.

In some embodiments of the device, the head receptacle comprises a bottom support surface, a back wall, side walls and a front wall, wherein the front wall is shorter than the back and side walls to support the neck of the subject. The front wall is adjustable in height to support the neck of the subject at different heights, and may be padded for the protection of the patient. The head receptacle is surrounded by a container that serves as the reservoir.

The system further includes catheters for placement in the aerodigestive tract of the subject and a pump for circulating liquid from the receptacle into the aerodigestive tract.

In other disclosed embodiments, the brain is cooled by direct external cooling of the head and cooling of blood that is delivered to the brain. The head is placed in a container that holds a reservoir of circulating cold liquid that externally cools the brain. Cold liquid is infused into the upper airway through catheters placed in the nasal cavity, oral cavity and/or upper chest to directly cool the inferior surface of the brain and the brainstem, and indirectly cool other areas of the brain by cooling blood that passes through the carotid and vertebral arteries. Delivering high volumes of cool liquid to the upper airway substantially fills the upper airway with the cool liquid and induces a turbulent flow of the liquid which then flows out of the nose and mouth and into the reservoir of cool liquid that is circulating around the head in the container.

In some disclosed embodiments, the head in the container is completely submerged in the cool liquid, with the liquid covering the nose and mouth to help completely fill the upper airway with the liquid.

A particular disclosed device or system for carrying out the method and cooling the brain includes a liquid container for receiving and maintaining the head of the subject at least partially immersed in cool liquid, and a source of cool liquid for absorbing heat to induce brain hypothermia. A plurality of liquid delivery catheters are connected to the source of cool liquid for insertion into the nasopharynx and oropharynx of the subject for direct delivery of cool liquid to those sites. A liquid circulation tube is also connected to the source of cool liquid and is placed in the container to circulate cooled liquid around the head of the subject in the container. Pumps are operatively associated with the device to move liquid from the container through the liquid delivery catheters and into the patient. The system cools the outer surface of the brain through the cranium, cools the inferior surface of the brain and brainstem through cool liquid delivered into the nasopharynx, and cools the blood perfusing the brain from the arteries of the mediastinum and neck (such as the internal carotid and vertebral arteries) through liquid delivered into the pharynx and/or esophagus.

The cool liquid can be maintained, for example, at a temperature of −30° C. to +20° C. to transfer heat from the brain at a sufficient quantity and at a sufficient rate to quickly induce hypothermia. Suitable liquids for this purpose include a perfluorocarbons, oils, and water mixtures containing salts and/or simple sugars and/or organic compounds (such as propylene glycol).

The source of cool liquid preferably provides sufficient liquid to substantially fill the upper airway (including the nasopharynx, oropharynx, hypopharynx, and proximal trachea) with the cool liquid. In other embodiments, the source of liquid is also sufficient to substantially fill the upper esophagus, entire esophagus, and/or stomach.

The foregoing and other objects, features, and advantages of the invention will become more apparent from the following detailed description, which proceeds with reference to the accompanying figures.

BRIEF DESCRIPTION OF THE DRAWINGS

FIG. 6B is a view similar to FIG. 6A, but showing a back support that has an upwardly included surface to elevate the upper thorax above the waist.

FIG. 7 is a view of another embodiment of the device in which a flat body support platform is fixed in, on or slightly above a large tub of cooling water with ice floating in it to cool the water in the tub.

DEFINITIONS

Figure 1A:
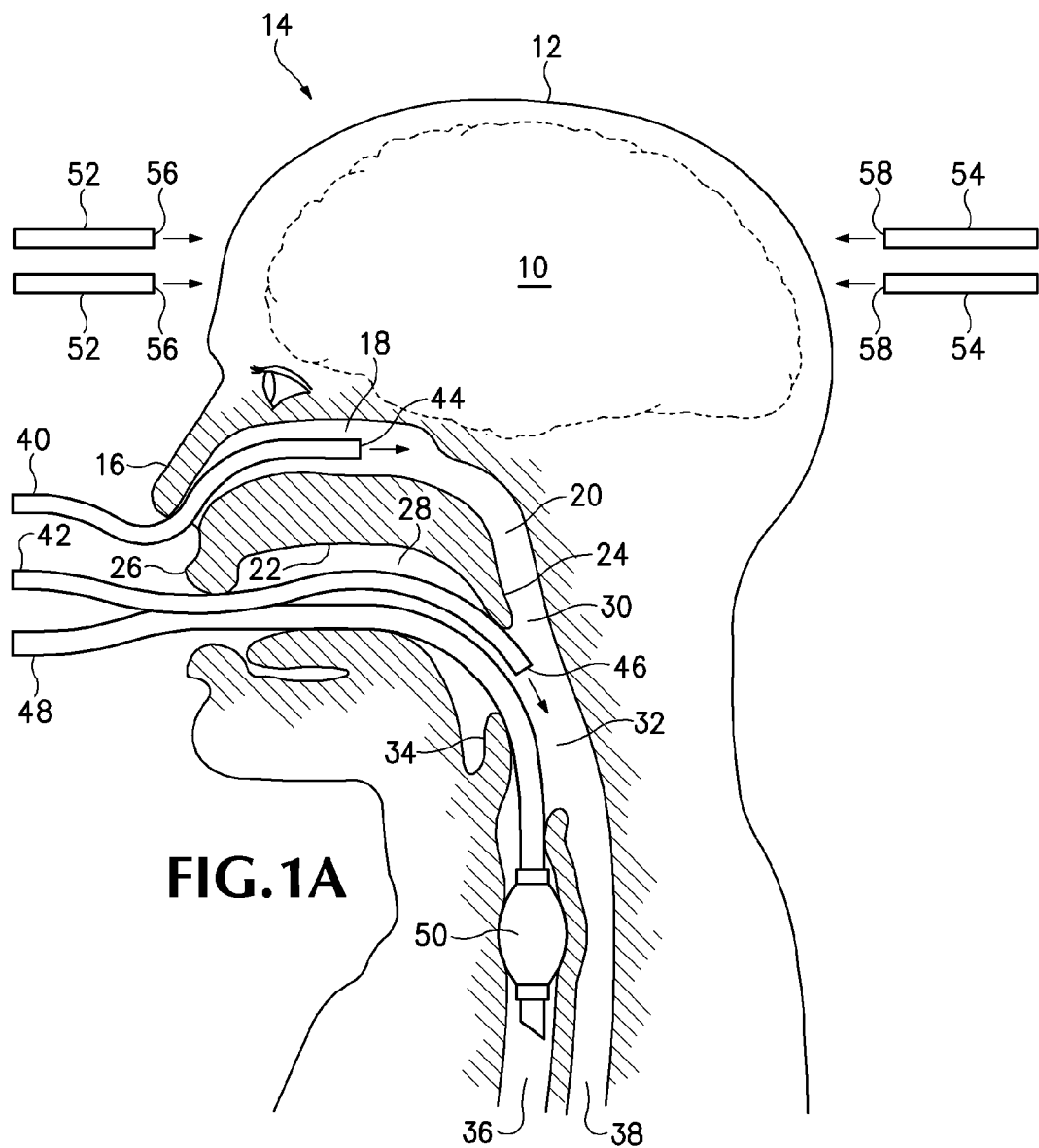
FIG. 1A is a schematic sectional side view of a human head and upper thorax with nasal and oral catheters inserted to perform high-flow irrigation of cooling liquid through the upper aerodigestive tract to achieve selective brain cooling. An endotracheal tube with an inflated cuff is shown inserted into the proximal trachea. External catheters apply turbulent liquid flow externally against the head.

"Aerodigestive tract" refers to a complex of organs that, in total, make up the tissues and organs of the upper respiratory tract and the upper part of the digestive tract. The aerodigestive tract, as used herein, is the lips and mouth, tongue, nose, throat, vocal cords, esophagus, stomach and trachea. The aerodigestive tract does not include the lungs or the intestines. "Introducing liquid into the aerodigestive tract" includes introducing liquids into any part of the aerodigestive tract, such as the nasal cavity, upper airway (nasal and oral cavity and pharynx), the nasal cavity and upper airway and esophagus, or the nasal cavity and upper airway and esophagus and stomach, or any combination or sub-combination thereof.

"Extension" of the neck refers to bending the neck to move the head posteriorly.

"Pharynx" refers to the part of the neck and throat situated immediately posterior to the mouth and nasal cavity, but superior to the esophagus, larynx and trachea. It is anatomically divided into the nasopharynx (posterior to the nasal cavity), oropharynx (posterior to the oral cavity) and hypopharynx or layngopharynx (between the oropharynx and the esophagus).

"Hypothermia" refers to a condition in which body or organ temperature is below normal physiological temperatures. "Therapeutic hypothermia" refers to hypothermia induced to attempt medical benefit in a subject. Inducing "selective hypothermia" does not require absolute selectivity; relative selectivity of cooling a target organ or area can occur. Hence inducing "selective hypothermia" refers to inducing hypothermia in a target organ or organs to a greater extent or substantially greater extent than in non-target organs. For example, selective hypothermia may be induced in the brain or head of a subject by selectively cooling blood vessels that perfuse that organ as well as selectively cooling anatomic structures that are contiguous with that organ. Selective hypothermia need not be absolutely selective, and some cooling of other organs (or the entire body) can occur. In particular examples, selective hypothermia reduces the temperature of the target organ (such as the brain) by at least 25%, 50%, or 75% more than the reduction of overall core body temperature. Inducing "non-selective hypothermia" refers to a generalized cooling of the body that is not specifically targeted to any particular organ (such as the brain). However, even with "non-selective" cooling some preferential cooling of a particular organ can occur.

A "non-nebulized" liquid is one that is not turned into a fine spray or atomized. The non-nebulized liquid therefore emerges in a continuous liquid stream instead of discontinuous droplets from a catheter. The continuous or coherent liquid flow provides superior turbulent flow that is not achieved by droplets, as well as greater flow rates (with consequently greater cooling rates) can be achieved by using non-nebulized introduction of cooling liquid into the aerodigestive tract.

"Turbulent flow" of liquid is agitated flow that is not strictly laminar. Turbulent flow helps disrupt liquid barriers and increases heat transfer as compared to laminar flow.

"Upper aerodigestive tract" refers to the portion of the aerodigestive tract above the esophagus. The "upper airway" refers to the air passageways above the trachea, which includes the nasal and oral cavities, as well as the pharynx.

References to "introducing a catheter" are understood to refer to introducing one or more catheters. For example, introducing a catheter into the nasal cavity can refer to introducing a catheter into each nostril so that there are two catheters in the nasal cavities.

DETAILED DESCRIPTION

A therapeutic system and method are disclosed for cooling the brain, spinal cord, or more generally the body of a subject to clinically beneficial temperatures that help preserve tissue function (such as brain function) following potentially tissue-damaging events, such as hypoxia (as can occur following cardiac arrest or respiratory failure), neurovascular events (such as a stroke), direct trauma (such as a closed head injury or spinal contusion) or perinatal insults (such as difficult deliveries). However, the treatment can be used for any person at risk of tissue injury or inflammation damage from a traumatic or other medical incident. The therapeutic method can be initiated prior to arrival at a medical center, but it is also suitable for in-hospital use.

The therapeutic method may be continued for hours or days as clinically needed and can be used with other methods of brain or body cooling. The therapeutic method can also be used as a bridge to concomitant therapies such as thrombolysis or thrombectomy for treating stroke and cardiopulmonary bypass for treating cardiac arrest. In the event of cardiac arrest, brain cooling may be initiated before or after spontaneous circulation is reestablished, and even when spontaneous circulation cannot be reestablished prior to presentation at a medical center. In some embodiments of the new method the brain is cooled (either separately or in combination) by two functional mechanisms: direct head cooling and cooling of blood that is delivered to the brain. The head is directly cooled externally by immersing it completely or partially in a container through which cold liquid circulates or by applying a turbulent flow of cold liquid externally against the head. Direct cooling of the inferior surface of the brain and brain stem are achieved by infusing cold liquid into the upper aerodigestive tract using catheters placed in the upper airway (for example into the nasal cavity, nasopharynx, oral cavity, oropharynx and/or hypopharynx). By establishing a continuous flow and exchange of liquid between the upper aerodigestive tract and the cool liquid (such as cooling liquid circulating around the head or present in a reservoir that does not immerse the head), a highly effective and more rapid internal cooling of the nasopharyngeal cavity, upper airway or aerodigestive tract occurs.

Cooling the upper aerodigestive tract and scalp causes blood delivered to the brain to be cooled as it flows through the arteries of the neck and head. Optional additional cooling of the upper chest is achieved by delivering cold liquid into the esophagus via a catheter inserted through the mouth with the tip positioned in the esophagus, for example the midesophagus. Alternatively, multiple outlet ports (either from a single or multiple catheters) can deliver even higher flows of cooling liquid in the esophagus. The outlet ports in the esophageal catheter(s) deliver the cold liquid into the proximal, and/or mid and/or distal esophagus, and/or the stomach.

In certain embodiments, the cool liquid circulating from the esophagus and upper airway/aerodigestive tract exits the mouth and mixes with the liquid surrounding the scalp, whence it is withdrawn from the container, optionally cooled and returned to the container, for example through liquid delivery catheters (such as the catheters in the nose, mouth and esophagus). Cooled liquid can be cooled and/or stored in a reservoir external to the head receptacle. In yet other illustrated embodiments described in greater detail below, the liquid can be cooled in the head receptacle without withdrawing it from the receptacle (the receptacle is the reservoir), by adding ice or other cold items to the liquid. In yet other embodiments, the cool liquid that passively flows out of the mouth and nose is returned to a cooling reservoir by the action of gravity, for example by passing through a liquid permeable net that support the head, or a drain in the receptacle that leads to the reservoir.

The initial temperature of the liquid is in the range of −30 to +30° C., for example −30 to +10° C. Optimal temperature may vary during treatment but is believed to be in the range of −20 to +10° C. Alternatively, the liquid is maintained at a temperature (such as a substantially fixed temperature) of less than +30° C., and in some embodiments less than +10° C., or even less than −10° C. (such as a temperature of about −17° C.). The liquid can be maintained at any constant temperature (for example within a range of ±2° C.) by circulating it between the receptacle/reservoir and a separate heat exchanger cooling unit, adding additional cool liquid as required or by adding cold objects to the reservoir of liquid. Alternatively the temperature is maintained by adding ice (including dry ice) or other cool objects at a specific temperature to the liquid.

Turbulent flow of the liquid over the surfaces of the scalp is achieved, for example, by constantly withdrawing the liquid to be cooled, and reintroducing the cooled liquid under pressure into the head receptacle, for example through a tube directed at the head. However other means of liquid agitation within the head receptacle may also be used. Turbulent flow over internal and external body surfaces improves heat transfer by reducing the depth of the boundary layer of immobile cool liquid. Hair may be removed if it has an insulating effect that interferes with effective rapid heat exchange.

One aspect of the cooling method is illustrated in FIG. 1A, which schematically shows the placement of irrigation catheters that deliver a flow of cooling liquid to structures that substantially selectively cool the brain 10 in the head 12 of a subject 14, as opposed to generalized induction of hypothermia throughout the body of subject 14. The sectional view shows (moving anterior to posterior) the nose 16 with nasal cavities 18 (only one shown) and nasopharynx 20. The bottom wall of nasal cavity 18 is defined by the palate, which is divided into the anterior hard palate 22 and posterior soft palate 24. Mouth 26 defines an entrance to oral cavity 28 which leads to a posterior oropharynx 30. Inferior to oropharynx 30 is hypopharynx 32 that is bounded anteriorly by epiglottis 34 and leads inferiorly to the anteriorly situated trachea 36 and posteriorly situated esophagus 38.

Targeted cooling of the brain is achieved by introducing a continuous or coherent flow of liquid that circulates through the upper airway, which is above the level of the trachea and esophagus, and includes the nasal and oral cavities 18, 28, nasopharynx 20, oropharynx 30, and hypopharynx 32. FIG. 1A provides an example of how to provide this continuous flow by introducing nasal catheters 40 into the nasal cavities and an oral catheter 42 into the oral cavity of subject 14. First and second nasal catheters 40 (only one is shown in FIG. 1A) are inserted into each nostril of nose 16 and advanced until the distal open delivery tip 44 is positioned in the nasal cavity above the hard palate 22 (although it can alternatively be positioned above either hard palate 22, soft palate 24, or even in nasopharynx 20). Oral catheter 42 is similarly inserted into the oral cavity 24 with the open delivery tip 46 advanced toward and positioned slightly beyond and below soft palate 24 with open delivery tip 46 positioned in oropharynx 32. To help isolate the lungs from the upper airway and aerodigestive tract, an endotracheal tube 48 is shown inserted through mouth 26 and hypopharynx 32 into trachea 36. An optional inflatable peripheral cuff 50 is shown in its expanded condition occluding the lumen of trachea 36.

The illustrated catheters 40, 42, 48 are single or multiple lumen catheters. The bores of catheters 40, 42 are of a sufficient size to permit a flow of a continuous or coherent column of cooling liquid through the catheters and out of open tips 44, 46 to establish the coherent flow of liquid that substantially fills the upper airway. One or more fronto-tempero-parietal catheters 52 are schematically shown in FIG. 1A positioned to direct a turbulent flow of cooling liquid against the anterior portion of head 12, for example against the fronto-parietal portions of the head, such as against the forehead or side of the head. One or more posterior catheters 54 are also situated to direct a turbulent flow of cooling liquid against a posterior portion of head 12, for example against the occipital portion of head 12. Catheters 52 have open tips 56 oriented within 1-5 cm of the surface of the head, and catheters 54 have open tips 58 similarly situation within 1-5 cm of the head surface.

Although not shown in the schematic illustration of FIG. 1A, each of the catheters is adapted for operative connection to a source of liquid for introduction through the catheter. Catheters 40, 42, 52, 54 are adapted for connection to a sufficient supply of cooling liquid of a temperature adequate to lower the brain to a targeted temperature (such as 33° C. or less), or by a targeted change in temperature within a set period of time (such as 5° C. within 30 minutes or less). Endotracheal tube 48 is adapted for operative connection to a ventilator or other source of respirable gas that can be introduced under pressure for mechanical ventilation of the lungs (not shown). Although the illustrated catheters are shown having end openings for discharging the liquid from the catheter into the aerodigestive tract, the catheters can instead be provided with multiple side holes in the distal 5-10 cm of the catheter to allow liquid to be discharged laterally from the catheter instead of (or in addition to) discharge from the tip. Lateral discharge helps promote turbulent flow within the aerodigestive tract.

Cooling liquid is introduced through tips 44, 46, 56, 58 of tubes 40, 42, 52, 54 as shown by arrows in FIG. 1A. In disclosed examples, the flow rate of the introduced liquid totals at least 5 L/min total from the combined flow of tubes 40, 42 that are situated internally (i.e. excluding external tubes 52, 54), but the combined flow rate from the internal tubes can be much higher, for example 5-50 L/min as described in greater detail below. The large volume of cooling liquid circulates through the upper airway/aerodigestive tract above the level of the esophagus and trachea, to at least partially fill the upper airway with the cooling liquid and assure substantial contact between the cooling liquid and the exposed surfaces of the upper aerodigestive tract/airway. In some embodiments, the upper airway and upper aerodigestive tract are substantially completely filled with the cooling liquid.

Many of the surfaces of the upper aerodigestive tract are irregular (such as the richly vascularized nasal turbinates) and the flow of liquid that bathes and moves along the irregular surfaces of the airway provides superior heat exchange to cool the airway. The turbulence induced by a large flow of liquid being introduced into the confined space of the upper aerodigestive tract and returning outside of any catheters or tubes through the airway itself further disrupts any insulative areas as the circulating liquid moves toward the mouth and nose. Liquid passively moves out of the mouth and nose as new cooling liquid replaced is in the upper airway to continuously replenish the cooling effect of the liquid.

Figure 1B:
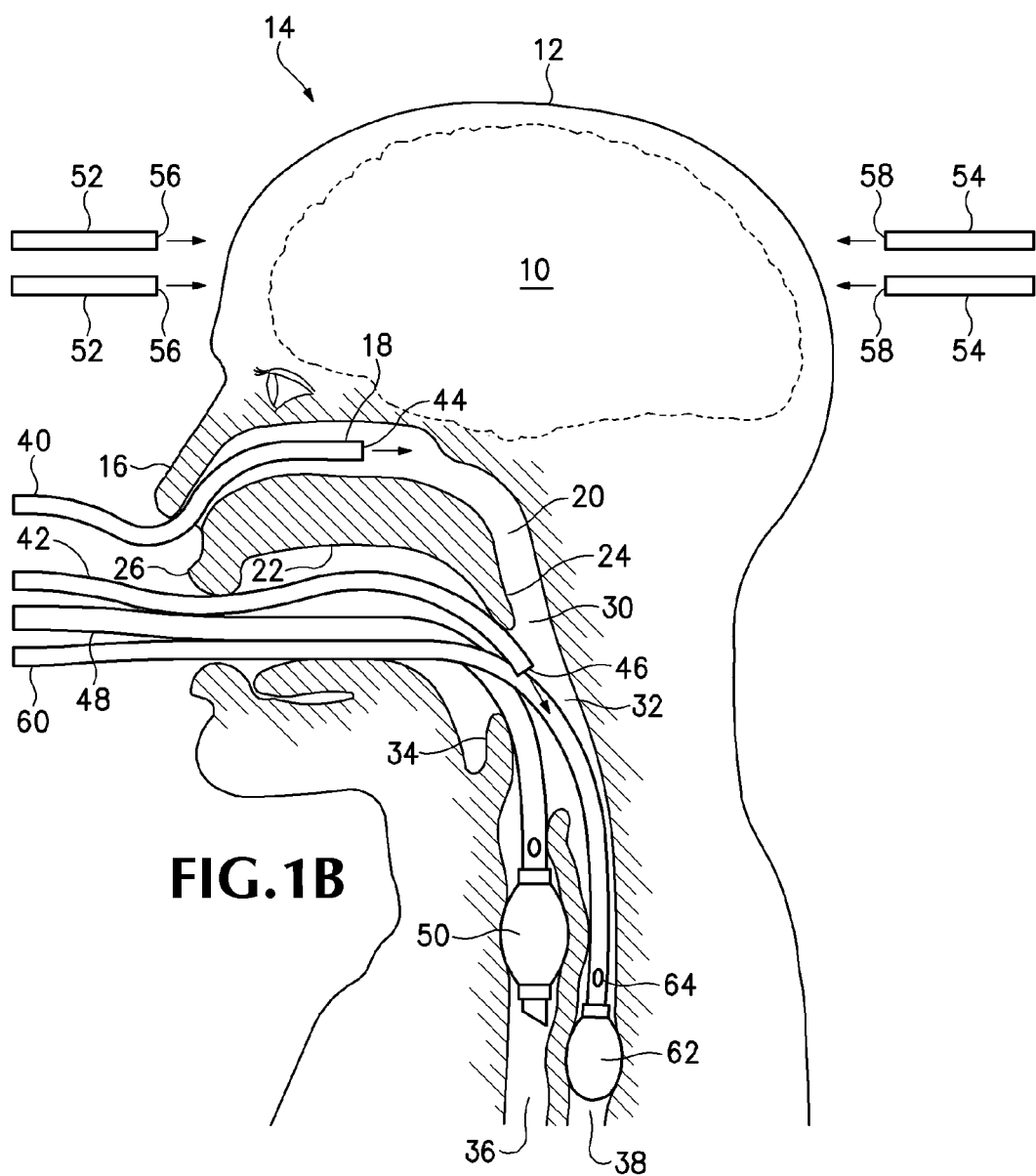
FIG. 1B is a schematic sectional side view of a human head and upper thorax, similar to FIG. 1A, but also showing a catheter obstructing flow into the esophagus.

FIG. 1B shows a variation of the method illustrated in FIG. 1B, wherein like parts have been given like reference numbers to those found in FIG. 1A. However, an esophageal tube 60 has additionally been inserted through mouth 26 into esophagus 38. Esophageal tube 60 has a distal balloon 62 that is shown in an inflated condition in the proximal or middle portion of esophagus 38 to substantially seal the esophagus beyond the balloon to the entry of cooling liquid into it. Esophageal tube 60 can be operatively connected to a source of cooling liquid (not shown) to introduce a flow of liquid under pressure that moves through the lumen of the catheter and emerges through side port 64 to thereby serve as an additional source of cooling liquid circulating through the upper airway.

The methods of cooling described in FIG. 1A and FIG. 1B are examples of "selective" cooling of the head and the brain in that cooling of those structures proceeds faster than cooling of other parts of the body. However a certain amount of non-selective cooling will also occur as well because the blood that perfuses the tissue of the scalp and upper aerodigestive tract will be cooled and returned to the heart thereby somewhat lowering systemic arterial blood temperature.

Figure 2A:
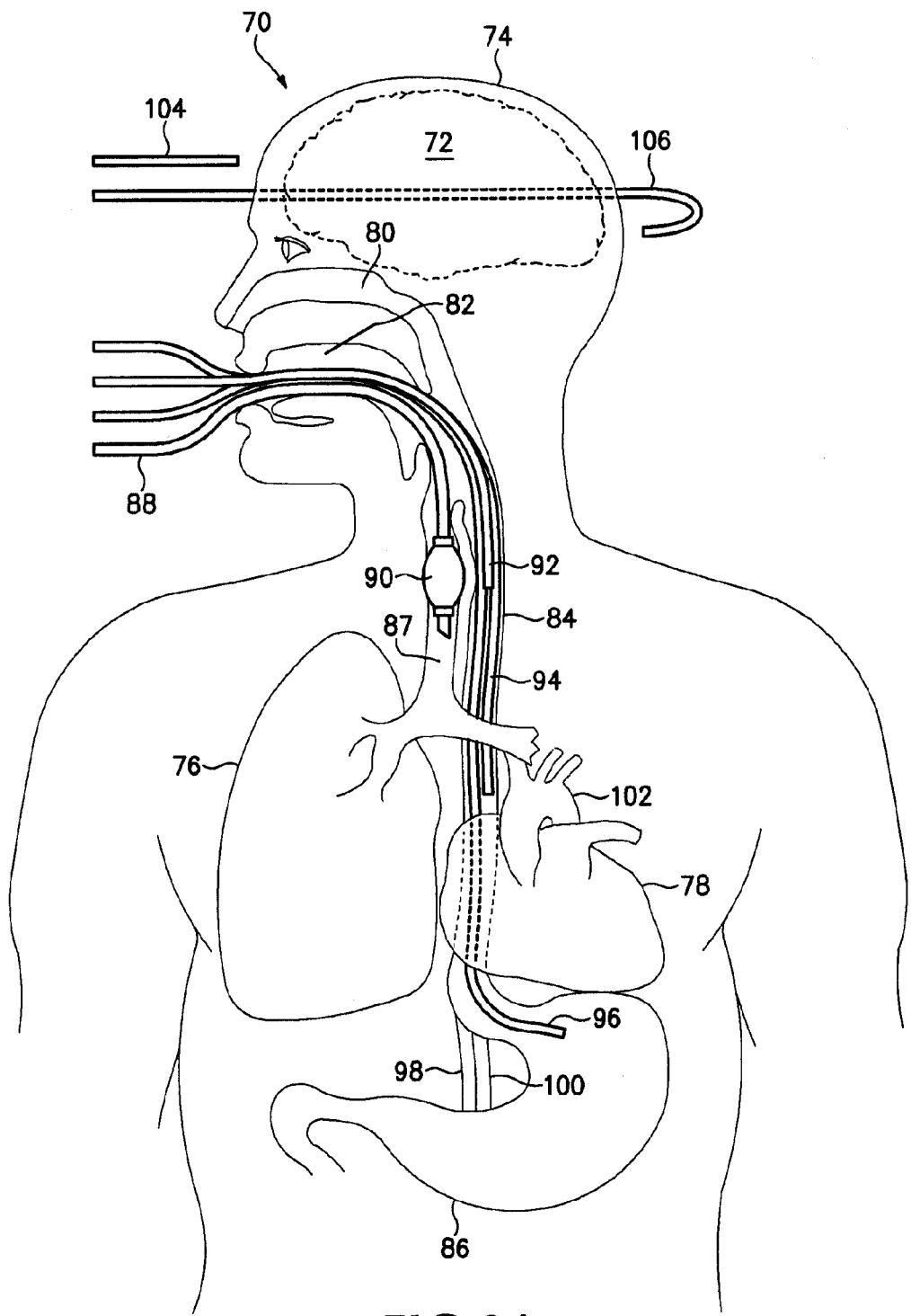
FIG. 2A is a view of the upper thorax and head, illustrating the placement of external irrigation tubes that direct a turbulent flow of cooling liquid against the face and head, and irrigation tubes that deliver a high flow of cooling liquid to the esophagus and stomach for inducing hypothermia in the body (without more selectively cooling the head and brain).

FIG. 2A illustrates a non-selective cooling method for inducing non-selective hypothermia in a subject 70 by generally cooling the body of the subject without specifically targeting the brain. FIG. 2A schematically shows the subject's brain 72, within head 74. One of the two lungs 76 is illustrated in the chest of subject 70, as is the position of heart 78. The subject's nasal cavity 80 and oral cavity 82 communicate with esophagus 84 and stomach 86, and trachea 87 that communicates with lung 76. No tubes are placed in nasal cavity 80, but an endotracheal tube 88 is positioned in trachea 87 with an optional inflated cuff 90 to isolate the lungs from the flow of cooling liquid in the upper aerodigestive tract. The esophagus and stomach are cooled by three esophageal tubes, namely an upper esophageal cooling tube 92 positioned with a single outlet in the upper esophagus, a middle esophageal cooling tube 94 positioned with a single outlet in the mid esophagus, and a gastric tube 96 positioned with a single outlet in the stomach for cooling the stomach. Although three tubes are illustrated in this example, a single multi-lumen tube with multiple outlet ports could alternatively be used. As previously described, side ports instead of end openings could also be used to increase turbulent flow.

Cooling liquid is introduced through all three tubes at the different levels of the digestive tract to provide primary cooling of the esophagus and stomach as the cool liquid returns from the stomach and esophagus. The cool liquid in the stomach contacts the rugae that greatly increase the surface area across which heat exchange with the blood can occur. Cooling liquid in the esophagus and stomach is also in close anatomic proximity to the inferior vena cava 98, superior vena cava (not shown), descending aorta 100, and aortic arch 102 to cool the blood therein as it moves through body, and particularly as it the blood moves through the structures of the mediastinum.

Although FIG. 2A only shows tubes inserted in the esophagus and stomach, it will be understood that cooling of the entire aerodigestive tract can occur by retroflow of cool liquid through the aerodigestive tract to the mouth and nose. In addition, irrigation catheters can be inserted in the mouth and nose as in FIG. 1A to further increase the flow of cooling liquid through the aerodigestive tract.

External liquid application tubes 104, 106 are positioned to apply a turbulent flow of liquid externally to the head of the subject. Tube 104 is positioned to flow liquid against the frontal area of the head (for example against the forehead) and tube 106 is positioned to provide turbulent flow in the occipital region.

Figure 2B:
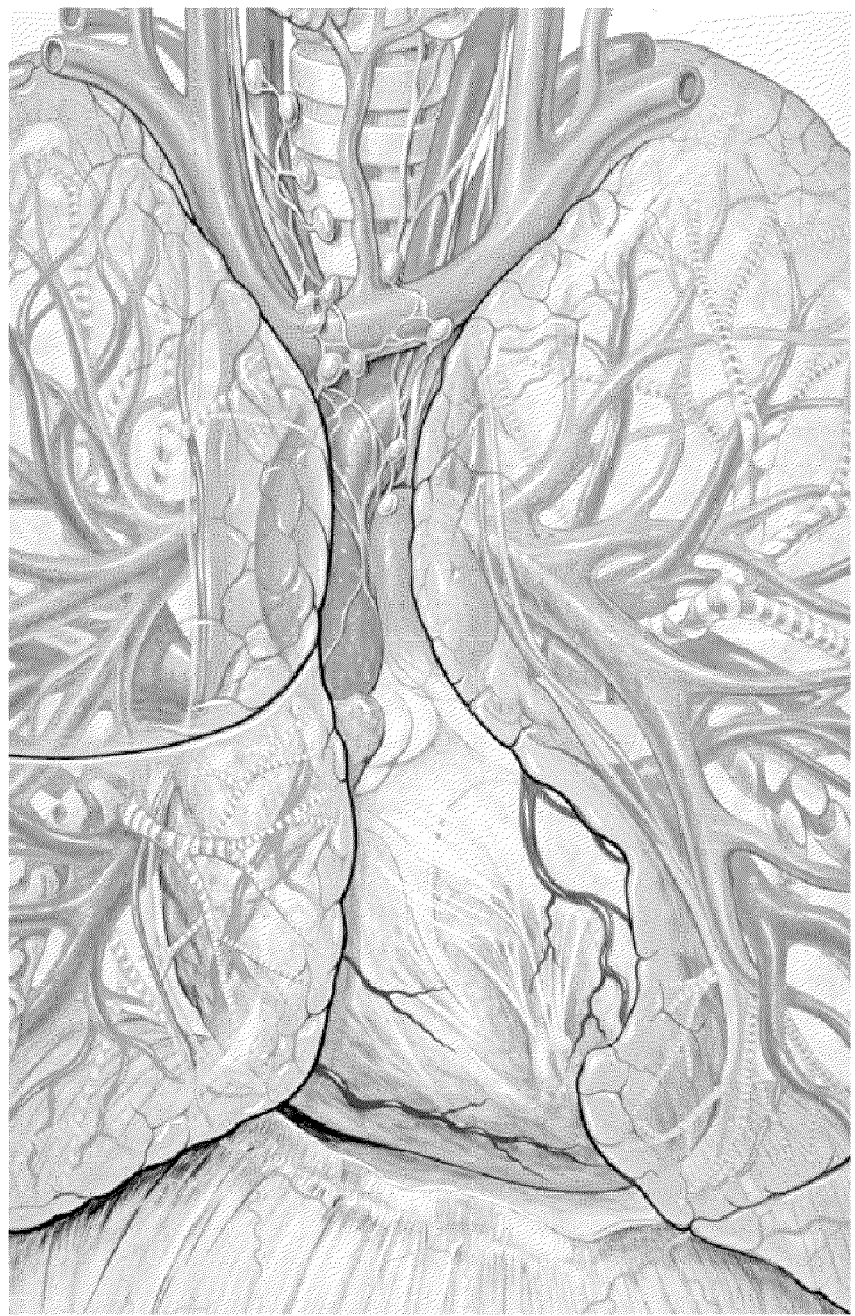
FIG. 2B shows the structures of the mediastinum that form a thermally insulated compartment that helps maintain mediastinal cooling induced by the methods and devices disclosed herein.

FIG. 2B illustrates that that the mediastinum is an anatomic compartment that is somewhat insulated and therefore retains the cooling effect of the liquid introduced through the esophageal tubes. The mediastium contains the heart, the great vessels of the heart, esophagus, and trachea, and is insulated laterally by the air-filled lungs and inferiorly by the stomach.

All of the cardiac output passes through the veins of the mediastinum. Internal cooling of the mediastinum can be accomplished by cooling the entire aerodigestive tract, from the nares to the pyloris (excluding lungs). The mediastinum is insulated from heat from the rest of the body by the lungs, larynx and stomach. The lateral aspects of the mediastinum are bordered by the lungs which of low mass and kept cool by the normal function of ventilation. The inferior aspect of the mediastinum is cooled by cooling the stomach and the superior aspect of the mediastinum, the neck, is cooled by cooling the upper airway. Insulation of the mediastinum enables cooling of the venous blood in the vena cava more efficiently than if similar cooling were to be performed on the vena cava within the abdomen. If vena cava cooling were attempted in the abdomen, heat from the surrounding organs would also be delivered to the vena cava and significantly impede cooling.

Figure 3:
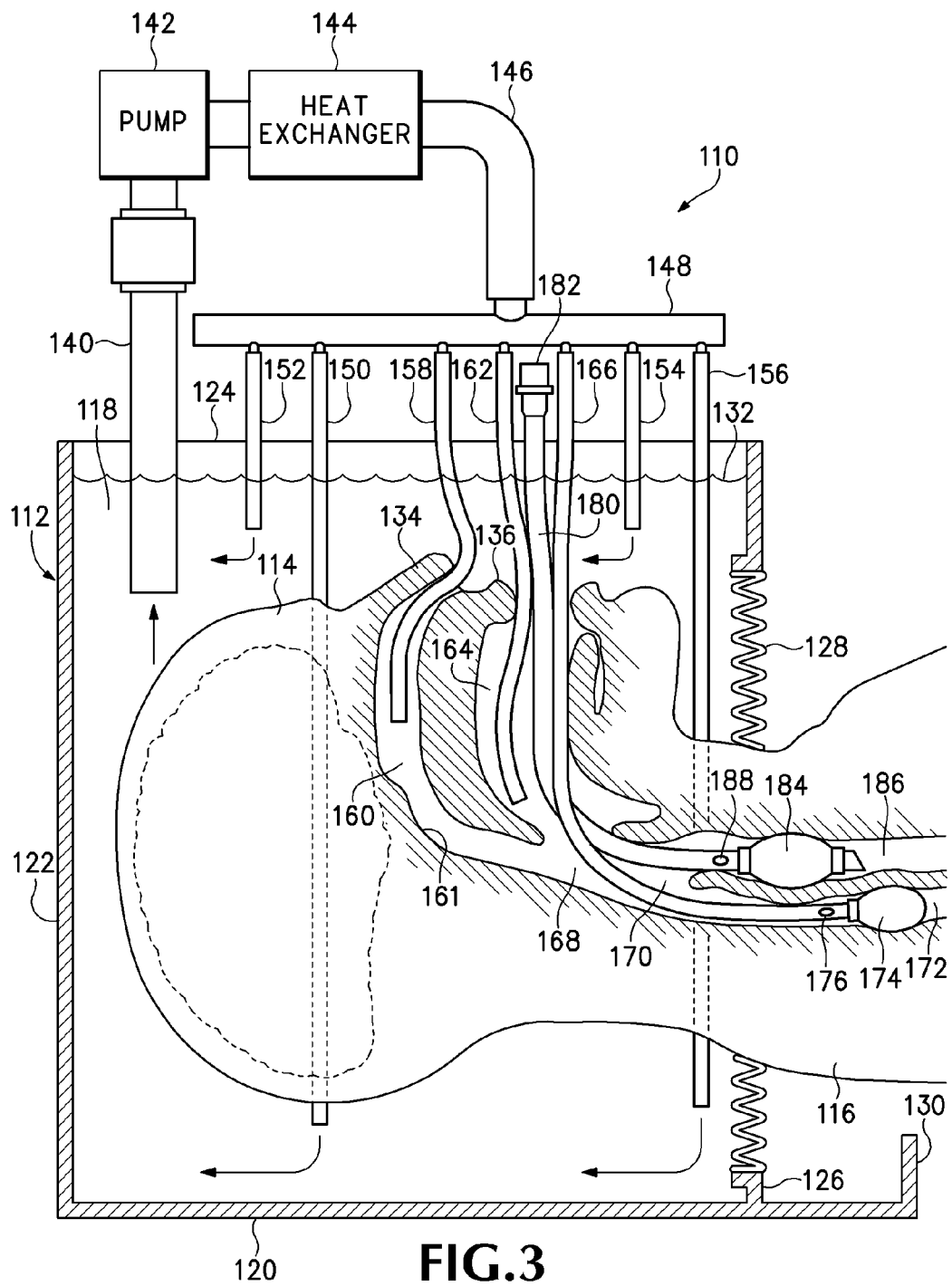
FIG. 3 is a partially schematic side view of the head of a supine subject placed in a container of cool liquid with liquid instillation and recirculation tubes inserted in the nose, mouth and upper esophagus, and an endotracheal tube in the trachea.

FIG. 3 provides an example of a more detailed brain cooling device 110 for carrying out the selective cooling method, wherein a container 112 encloses a head 114 of a subject 116 who is in a supine position (with the face up). Head 114 can be partially or totally immersed in cool liquid 118, but the illustrated embodiment shows total immersion of the head and face. The illustrated container 112 is a rectangular or square box having a solid flat bottom wall 120, three solid upright side walls 122 (only one is shown in FIG. 1), and open top face 124. Side walls 122 are connected to bottom wall 120 and each other with liquid tight seals. The bottom wall 120 and three solid upright side walls 122 and the upright solid wall 126 that receives the neck may, for example, be preformed out of contiguous material, as in a seamless unitary piece of molded plastic. Open top face 124 defines a square or rectangular opening large enough to provide access to the entire face. An upright side wall 126 defines a neck receiving opening that contains an annular flexible seal 128 to inhibit flow of liquid from container 112. An overflow trough 130 may extend along the bottom edge of face 126 to collect liquid that leaks through the seal, and re-circulate it to the container by a recirculation pump (recirculation tubing not shown). In the illustrated example, the dimensions of the container are 35 cm for length, width and height for an adult sized box and 20 cm on all sides for a device to be used for infants.

The reservoir of cool liquid 118 can substantially fill container 112. The liquid in the box has a top liquid level 132 that in the illustrated embodiment is within 2-10 cm of the top edge of the box, such that the liquid completely submerges head 114 below liquid level 132. With the liquid at this level, both the nose 134 and mouth 136 of subject 116 are completely covered with liquid, and the upper airways can passively fill with liquid from the container in addition to being actively filled with liquid pumped into the airway, as described below. The area around the head and in the upper airways is therefore a substantially uninterrupted continuum of cooling liquid that establishes efficient thermal exchange with the anatomic structures that come into contact with the continuum of liquid.

Device 110 is provided with a cooling means for controlling the temperature of the liquid in container 112. The cooling means can take many forms, such as making the container itself a refrigeration unit, adding cool objects (such as ice) to the liquid, and using endothermic chemical reactions (such as ammonium nitrate in water) in the walls of the container to cool them. However, in a particularly illustrated embodiment liquid in container 112 is cooled externally to the container by pumping it from the container to a heat exchanger 144 where it is cooled, and then pumping it back to the container. The heat exchanger can be of any type, such as a shell and tube heat exchanger, a plate heat exchanger, a regenerative heat exchanger, an adiabatic wheel heat exchanger, a fluid heat exchanger, or a dynamic scraped surface heat exchanger. Additional information about such devices is readily available, for example in Sadik Kakaç and Hongtan Liu *Heat Exchangers: Selection, Rating and Thermal Design,* 2nd Edition, CRC Press (2002)(ISBN 0849309026).

FIG. 3 shows an intake conduit 140 that extends from container 112 to a liquid pump 142. A heat exchanger 144 is in series with pump 142, and an outlet conduit 146 extends from heat exchanger 144 and communicates with an elongated distribution conduit 148 that provides multiple catheter connection outlets. Although the illustrated embodiment shows a single pump, more than one pump can be used. The pump can also be manually operated (for example by manually rotating or reciprocating a pump handle) or non-manually operated (for example by actuating an electrically operated pump).

Liquid circulation conduits of various lengths are connected to the outlets on distribution conduit 148 and extend through the open top face 124 of container 112. Four of them are liquid circulation tubes 150, 152, 154, 156 which ensure turbulent flow of liquid to the scalp and face. Tubes 150 and 156 are long tubes that reach almost to the bottom of container 112 for deep recirculation of liquid, while tubes 152, 154 are shorter and extend only into the top portion of container 112 to provide more superficial recirculation of liquid in the container. Another of the liquid circulation conduits is a first liquid delivery catheter 158 for delivering cool liquid to the nasal cavity 160 of the subject, and it is of sufficient length to extend from distribution conduit 148 to a distance of about three to six cm into the nasal cavity of a head 114 in container 112, with the outlet of catheter directed at nasopharynx 161. Another of the conduits is a second liquid delivery catheter 162 for delivering cool liquid to the oral cavity 164 of the subject. Catheter 162 is of sufficient length to extend a distance of about six to twelve cm into oral cavity 164 with its outlet directed at oropharynx 168.

A third liquid delivery catheter 166 is similar to a nasogastric tube, and extends from distribution conduit 148 and is of sufficient length to reach into oral cavity 164, through oropharynx 168, hypopharynx 170 and into esophagus 172. Typically, catheter 166 is of a sufficient length for it to extend 25 to 30 cm past the lips. Catheter 166 is a multi-lumen catheter provided with a balloon tip 174 that is selectively inflatable, for example using a source of pressurized air such as a syringe (not shown) that introduces the air through one of the lumens to the balloon tip 174. Another lumen of catheter 166 opens to a side port 176 that communicates with distribution conduit 148 for delivering cool liquid into the proximal esophagus. Side port 176 is proximal to balloon tip 174, so that when balloon tip 174 is inflated the liquid delivered into esophagus 172 will not flow into the distal gastrointestinal tract (such as the stomach), but will instead move in a proximal direction through the upper airways and eventually circulate to and rejoin the reservoir of liquid in container 112.

The disclosed brain cooling system also employs an optional multi-lumen endotracheal tube 180 having a conventional coupling collar 182 for connection to a source of ventilation (not shown). Suitable sources of ventilation include any device for introducing under positive pressure a non-toxic fluid (such as a gas) with oxygen in it. Examples of such sources include a manual ventilation bag or a mechanical ventilator that communicate with the primary lumen of tube 180 for delivering the gas into the lower airways and lungs. Endotracheal tube 180 includes a conventional distal cuff 184 that can be selectively inflated after insertion by introducing fluid under pressure (such as gas from a syringe) through a secondary lumen of tube 180 to secure the tube in place within the trachea 186, provide an effective seal between tube 180 and the walls of the trachea that improves the efficiency of ventilation, and inhibit the entry of liquid from the upper airway into the lower airways and lungs.

Although the illustrated embodiment of endotracheal tube 180 in FIG. 3 includes cuff 184, the cuff is not always required to substantially seal the airway, for example in small or pediatric subjects in whom the endotracheal tube itself is large enough to effectively occlude passage of liquid between tube 180 and the walls of trachea 186. In the illustrated embodiment (FIG. 3) a suction port 188 is located on the side of tube 180, proximal to cuff 184. Port 188 communicates with a tertiary lumen in tube 180 and is connected to a source of negative pressure (not shown) that withdraws liquid from the trachea. The removed liquid can be recirculated into the reservoir of liquid 118 in container 112.

In use, head 114 of subject 116 in need of brain cooling is placed in container 112 by inserting head 114 through flexible seal 128. A more liquid-resistant seal with the neck is provided by placing a thickened liquid-resistant emulsion or gel (such as petroleum jelly) externally in a continuous ring around the neck. A soft, liquid-resistant foam strip is also placed around the neck and may be layered to achieve a desired thickness. Flexible seal 128 achieves a tightness around the neck that is sufficient to provide a substantially liquid-tight seal but not so tight to obstruct arterial or venous flow of blood through the neck. In some embodiments, a plastic liner (not shown) is also placed in container 112 around head 114 to provide an additional barrier to loss of liquid from container 112.

The subject 116 may optionally be prepared for the brain cooling procedure by removing hair from the head, for example by cutting the hair or shaving the head to improve conductive loss of heat externally from head 114 to surrounding cool liquid 118. If the subject is conscious, sedation may also be administered (for example intravenously administering a benzodiazepine or narcotic) to lower the level of consciousness and/or induce transient amnesia about the procedure. Once the subject's shaved head 114 is positioned within container 112, unobstructed access to the interior of the container is provided by the completely open top face 124 of container 112. Deep circulation tubes 150 and 156 are positioned around head 114 with their outlets proximal to bottom wall 120. Superficial circulation tubes 152, 154 are positioned above head 14 with the outlets of tubes 152, 154 directed at the face and scalp of subject 116. Catheter 158 is lubricated in a conventional fashion and inserted through a nostril to a distance of three to six cm into nasal cavity 160 so that the tip of catheter 158 is adjacent the vascularized surfaces of the turbinate mucosa and near the cribiform plate of the ethmoid bone that supports the inferior surface of the cerebral cortex, with the outlet of catheter 158 directed at nasopharynx 161. Esophageal catheter 166 is inserted through the mouth (to a distance of 25 to 30 cm past the lips) into the proximal esophagus 172, and once it is in position cuff 174 is inflated. Endotracheal tube 180 is inserted into trachea 186 and cuff 184 inflated. The tertiary lumen of endotracheal tube 180 is connected to suction.

Pre-cooled liquid that is already at the desired temperature is introduced into container 112 until the liquid level 132 is above the intake level of intake conduit 140. Liquid is circulated by activating pump 142 which draws liquid from container 112 though conduit 140 and propels it under pressure, for example a pressure of about out 20-60 cm $H_2O$ through heat exchanger 144, outlet conduit 146 and into distribution conduit 148. The liquid is then distributed among the outlets through the series of conduits that lead to container 112. Turbulent flow is induced in container 112 around the head by introduction of cool liquid through circulation tubes 150, 152, 154 and 156. This turbulent flow helps disrupt convection boundaries that would otherwise form at the surface of the head or face.

Pump 142 also circulates the cool liquid through tube 158 into the nasal cavity, through tube 162 into the oral cavity, and through tube 166 and out of port 176 to introduce cool liquid into the proximal esophagus. The liquid introduced through the tubes merges with cool liquid that passively enters from the reservoir of liquid in surrounding container 112 to substantially fill the upper airways with a turbulent flow of cool liquid that is in an uninterrupted liquid continuum with the reservoir of cool liquid around head 114. A continuous recirculation of liquid from the upper airways to the reservoir of liquid around the head and back into the upper airway occurs, and the liquid may also be continuously cooled to maintain it at a desired temperature that induces rapid cooling of the brain to a desired therapeutic temperature.

As previously noted, the neck of the subject rests in an opening through one wall of the container. The opening is provided with a sealing means, such as a circumferential flexible sealing material that circumscribes the neck to help provide a more liquid-tight seal. The liquid-tight seal around the neck can include a thickened liquid-resistant emulsion or gel (such as petroleum jelly) that is applied to the skin to make a continuous ring around the neck. A soft liquid-resistant foam strip may be placed around the entire circumference of the neck (for example over the gel) and may be layered to achieve a desired thickness. Finally, the flexible sealing material is tightened around the neck to a pressure sufficient to provide a substantially liquid tight seal but not tight enough to obstruct arterial or venous blood flow in the neck.

In one embodiment, the neck-receiving opening is a "U" shaped opening in the side wall 126 of container 112, and the width of the "U" is wider than the neck.

Attached to the inner edges of the opening is a liquid-resistant flexible material (such as rubber or vinyl). At least 2 inches of free material extends from the inferior aspect of the defect and sufficient material extends from each lateral aspect of the defect to cross completely to the other side of the opening. To finish the seal around the neck, the excess material superior to the anterior surface of the neck is held together by clips. The excess material from both sides is wrapped around each other before being temporarily clipped together.

Figure 4:
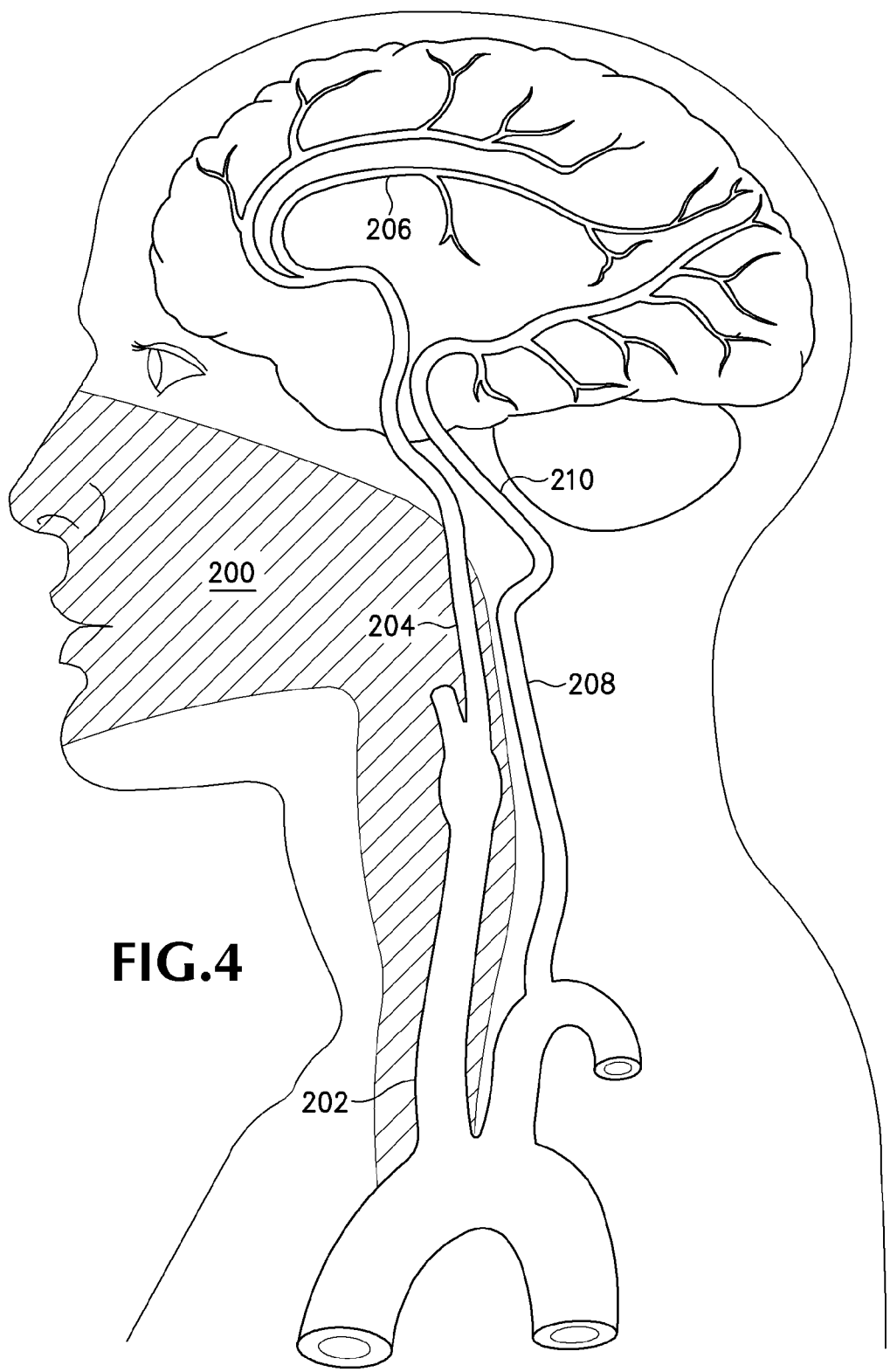
FIG. 4 is a schematic side view of the head, neck and chest of a subject illustrating the upper airway and some of the blood vessels that are cooled by circulating cool liquid through the aerodigestive tract during selective cooling of the brain.

FIG. 4 shows a shaded area that corresponds to the upper airway that is filled with cool liquid, and this area includes the nasal cavity, nasopharynx, oral cavity, oropharynx, and hypopharynx. The upper airway is defined by the walls of the pharynx that are laterally flanked in close association on either side by major blood vessels that perfuse the brain. As shown in FIG. 4, these blood vessels include common carotid artery 202 and internal carotid artery 204, which in turn supplies anterior cerebral artery (not shown) and middle cerebral artery 206. Another blood vessel in close anatomic association to the upper airway includes the vertebral artery 208, which is a branch of the subclavian artery and that in turn forms the basilar artery 210 that supplies blood to the vertebrobasilar system. The blood flowing through the arteries of the neck are conductively cooled by their close association with the cool liquid that fills the upper airway, and this cooled blood quickly lowers the temperature of the brain as the blood perfuses it.

Further cooling of the blood that perfuses the brain is achieved by the introduction of cool liquid into the proximal esophagus where the cool liquid comes into closer contact with mediastinal and lower neck structures, including the common carotid artery 202.

In this novel therapy, cooling of the blood starts in the aortic arch if there is cold liquid flow in the esophagus and continues throughout the length of the common and internal carotid arteries which are in close proximity to the upper airway filled with circulating cold liquid. The posterior circulation (vertebral and basilar arteries) is also cooled. Cooling continues in the Circle of Willis itself which is separated from the upper airway by a thin layer of soft tissue and bone. Direct cooling of the scalp and upper airway also results in a temperature gradient within the brain, with surface temperatures colder than deep in the brain. This gradient is offset by flowing blood since the cerebral arteries traverse long distances along the relatively cooler surface of the brain before delivering cooled blood to deeper brain structures.

Using the disclosed method, focal or isolated cooling of the head/and or brain is achieved without the adverse physiological and medical consequences or technical difficulties of cooling the entire body or large portions of it. Brain cooling can continue for a sufficient period of time to avoid damage to the brain, and this period can extend for minutes, hours, days or weeks. In some embodiments, the cooling continues for at least 24 hours, at least 48 hours, at least one week or longer. The period of time during which cooling is continued is determined by the condition of the patient and the clinical judgment of medical personnel. The temperature of the cool liquid can be changed over time in accordance with therapeutic needs. For example, the liquid may initially be cooled to 10° C. or less (for example less than zero ° C.) to induce rapid brain cooling and inhibit the development of brain edema, adverse metabolic changes or reperfusion injury. After the first few hours or even days of use, the temperature of the liquid can be increased, for example to 20-30° C., to cool the brain with a lesser risk of hypothermic damage to soft tissues.

This method can produce cerebral cooling in an estimated 5-15 minutes compared to 3-5 hours demonstrated in human studies with many other prior art hypothermic treatments. Therapy may be started in the field (outside a hospital setting) to accelerate the initiation of treatment and reduce the elapsed time to achieving the temperature goal following the onset of illness. The devices and methods can be used by someone having only basic emergency medical skills, such as the ability to place the catheters and insert an endotracheal tube. The simplicity of the method will also allow for rapid application of treatment in a broad array of clinical situations. The cool liquid can be significantly cooler than ice water used in previous human studies and most animal studies, thereby providing a large temperature gradient that promotes deeper and more rapid brain cooling.

Combining the scalp, upper airway and cerebral blood cooling provides rapid and effective cerebral cooling. The method is particularly effective because it cools all of these structures using a common pool of circulating cold liquid. This method of aggressive local cooling is believed to be effective at rapidly cooling the brain even in the absence of spontaneous circulation, although circulating blood is believed to further accelerate the cooling. The disclosed method also permits deeper levels of hypothermia to be achieved, which may help to realize the possible benefits of "suspended animation." This treatment also leaves open the possibility of salvaging life and neurological function even in those who do not achieve restoration of spontaneous circulation in the field. After arrival at an appropriately equipped medical center, whole body and brain blood flow can be reinstituted using cardiopulmonary bypass while more aggressive and time consuming attempts to restore and maintain spontaneous circulation are explored. If the brain is cooled, greater neurological recovery can be achieved even if the restoration of circulation is significantly delayed.

The circulation of cool liquid around the head is also believed to be more effective than the static application of a cold source (such as a cold pack or skull cap). Factors that functionally insulate the scalp from local hypothermia treatment include scalp hair, the boundary layer effect, and layers of material and air between a cold helmet and the scalp. The direct contact of scalp structures with the circulating liquid helps avoid these problems.

Direct cooling of the inferior surface of the brain is believed to occur more rapidly than scalp cooling due to thinner boundary layers of bone and soft tissue. Bone between the upper airway and the brain is approximately half as thick as bone in the scalp and the soft tissue layer is ¼ the thickness of the scalp.

Figure 5A:
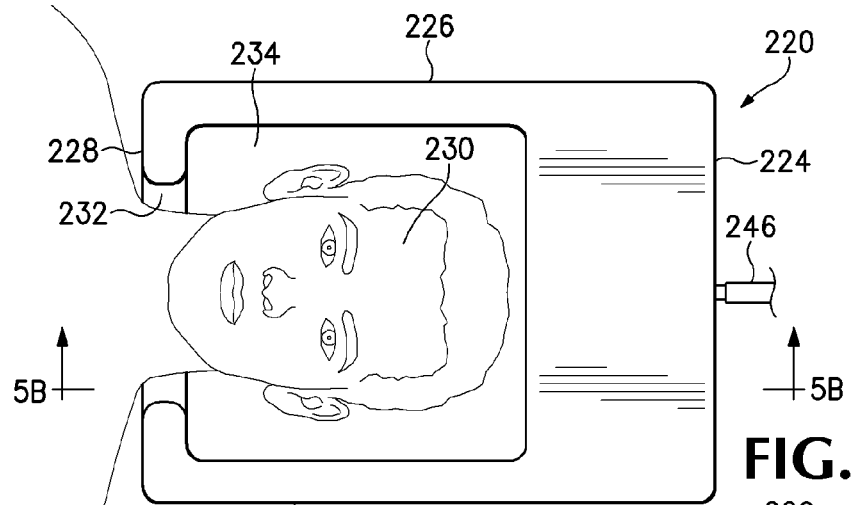
FIG. 5A is a top view of a head receptacle with a surrounding cooling liquid reservoir, with a head of a subject placed in the receptacle.
Figure 5B:
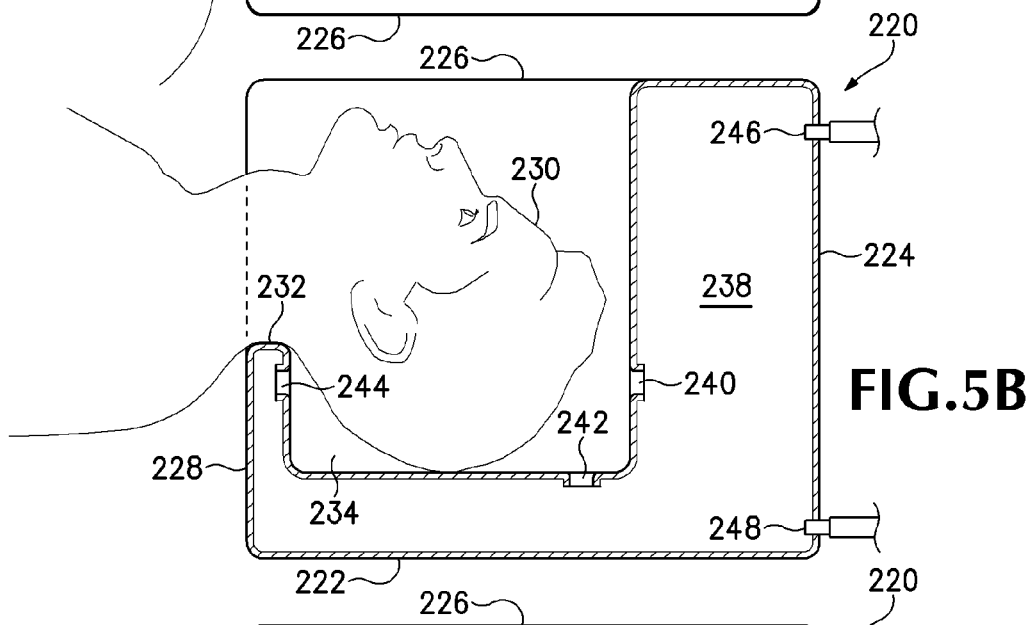
FIG. 5B is a side-view of FIG. 5A illustrating extension of the neck of the subject.
Figure 5C:
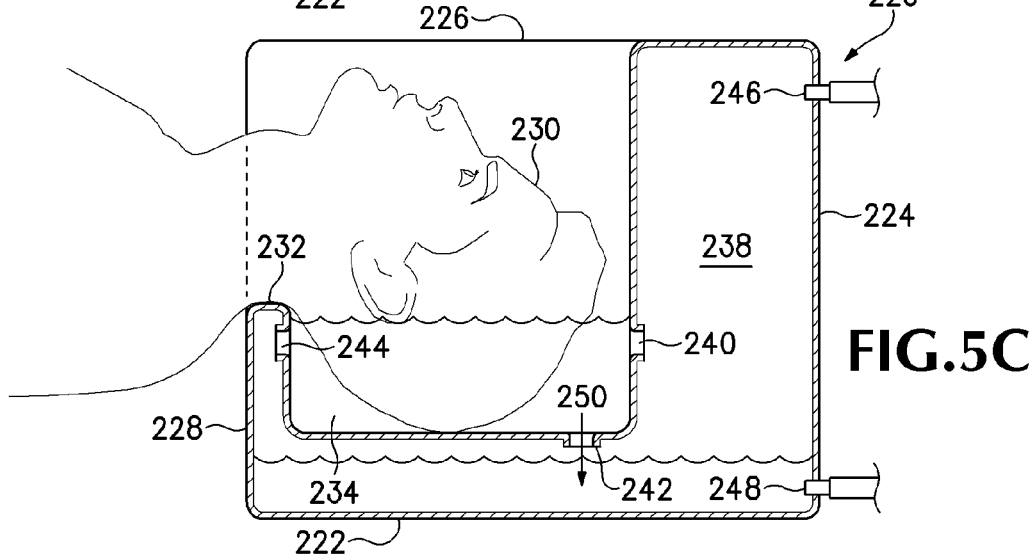
FIG. 5C shows the device in use, with cooling liquid filling the receptacle.

An additional example of a device suitable for use with either selective or non-selective cooling is shown in FIGS. 5A-5C. The device is a head cooling box 220 having a rectangular base 222, a rectangular rear wall 224, two opposing side walls 226, and a front wall 228. Each of walls 224 and 226 are sufficiently high to extend above the head 230 of a subject within the box, even when the head is tilted with the head in extension as in FIGS. 5A-5C. However front wall 228 has a cut-out support portion 232 (FIG. 5A) for receiving the neck of the subject.

Spaced from and parallel to the outer walls of box 220 are a set of inner walls that form a head receptacle 234 that is sufficiently large to receive the head 230 as shown in FIGS. 5A-5C, with the neck of the subject resting on support portion 232. Between the head receptacle and the outer walls the box forms a reservoir 238 that partially or completely surrounds receptacle 234 for storing a sufficient volume of cool liquid to circulate through the subject and to be applied externally against the scalp. Reservoir 238 extends behind and below receptacle 234 and communicates with receptacle 234 via one or more openings that form drains 240, 242, and 244. In the illustrated embodiment, drain 240 is in a rear wall, drain 242 in a bottom wall, and drain 244 in a front wall of receptacle 234. An upper port 246 extends through rear wall 224 near the top of box 220, and a lower port 248 extends through rear wall 224 near base 222 of box 220.

In use, the head 230 of a subject in need of treatment is placed in box 220 with the neck in cut-out portion 232 and the head tilted back in extension. Cool liquid is introduced into reservoir 238 to provide a large volume of cool liquid that can then be circulated though irrigation catheters (not shown) into the aerodigestive tract of the subject as described earlier. The cool liquid is initially delivered into reservoir 238 through upper port 246, and is subsequently withdrawn through lower port 248 and returned through drains 240 and/or 242 and/or 244 after coming into contact with the subject. As liquid is introduced into the aerodigestive tract, it flows into and through the aerodigestive tract until it eventually passively exits the mouth and nose of the subject without being suctioned or removed through a catheter or other tubing. As the liquid emerges from the mouth and nose, it collects in receptacle 234 around head 230 to further cool the head externally to lower brain temperature and drains into reservoir 238 via drains 240-244. The rate at which liquid can return from receptacle 234 to reservoir 238 through one of more of the drains is adjusted by the degree to which the drains are opened, and the position and number of open drains. In the illustrated embodiment of FIG. 5C, bottom drain 242 is open while side drains 240, 244 are closed so that liquid in receptacle 234 passively flows under the influence of gravity into the underlying portion of the reservoir, as shown by the arrow 250. Adjusting the rate a which liquid drains from receptacle 234, relative to the rate at which liquid enters the receptacle, determines the level of liquid in receptacle 234.

In the illustrated embodiment of FIG. 5C, the liquid level in surrounding reservoir 230 is lower than the level of bottom drain 240, which permits drainage through bottom drain 242. However, in those instances in which a larger volume of cool liquid is provided in surrounding reservoir 238, the liquid is still maintained at a level below side drains 240, 244 which are open (while bottom drain 242 is closed).

Figure 5D:
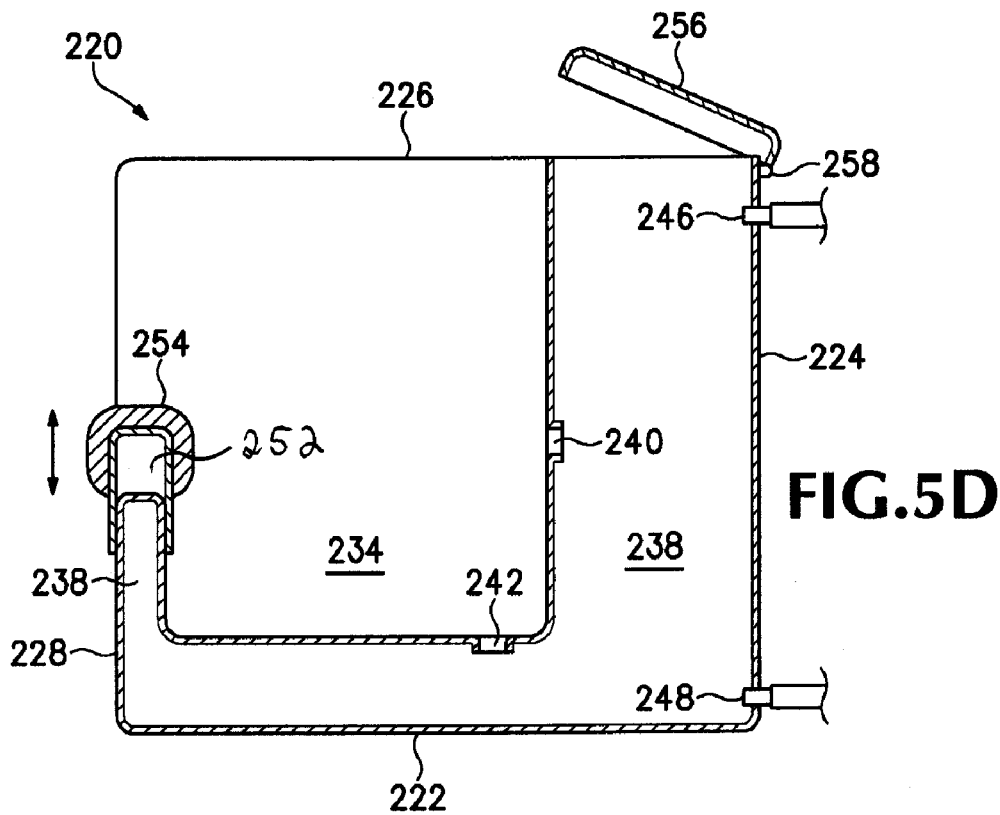
FIG. 5D shows an alternative version of the device with a front wall having an adjustable height for supporting the neck of a subject in different degrees of neck extension.
Figure 5E:
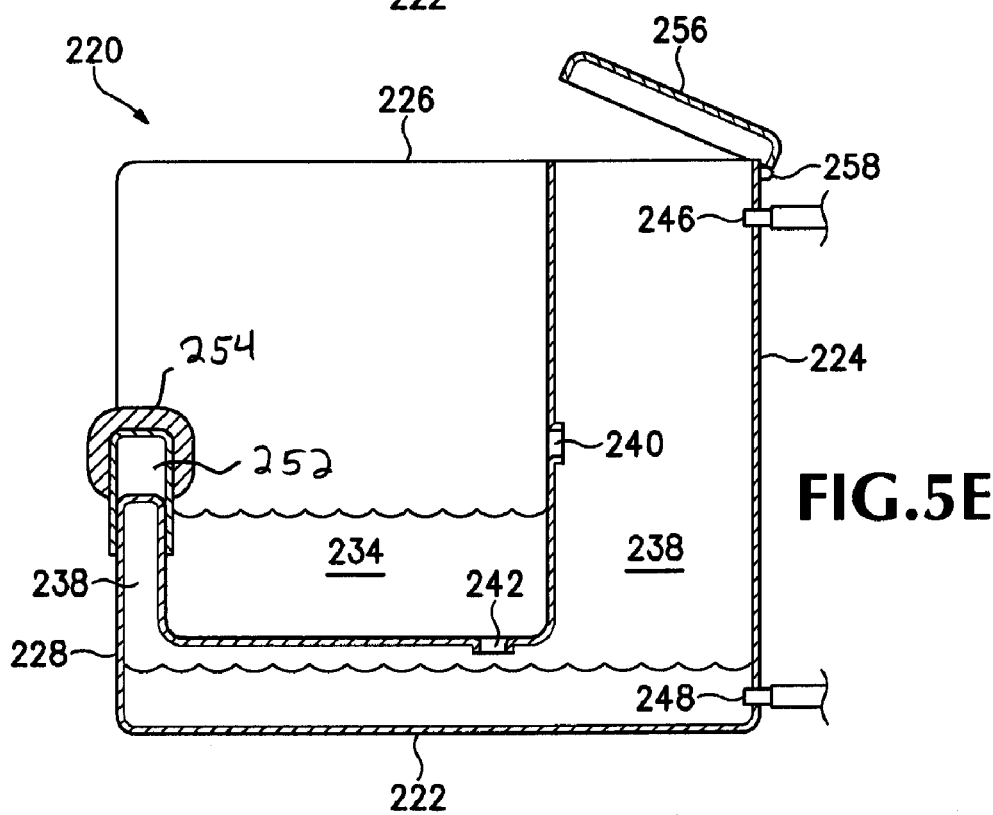
FIG. 5E shows the device of FIG. 5D with the head receptacle filled with cooling liquid.

An alternative embodiment is shown in FIGS. 5D and 5E, in which corresponding parts from FIGS. 5A-5C are given like reference numbers. This embodiment differs from the prior version, however, in that the front wall 228 has a height adjustment member 252 that fits on front wall 228 and can be moved toward and away from base 222 to adjust the height of the support for the neck of a subject. Adjustment member 252 is capped with a cushion 254 for protection of the neck of the subject and allows for a variable amount of neck extension. The top of reservoir 238 is also covered by a lid 256 that pivots at hinge 258 to open and close reservoir 238. The reservoir may be opened, for example, to add ice or other cold objects to reservoir 238 when cooling of liquid within it is desired.

Figure 5F:
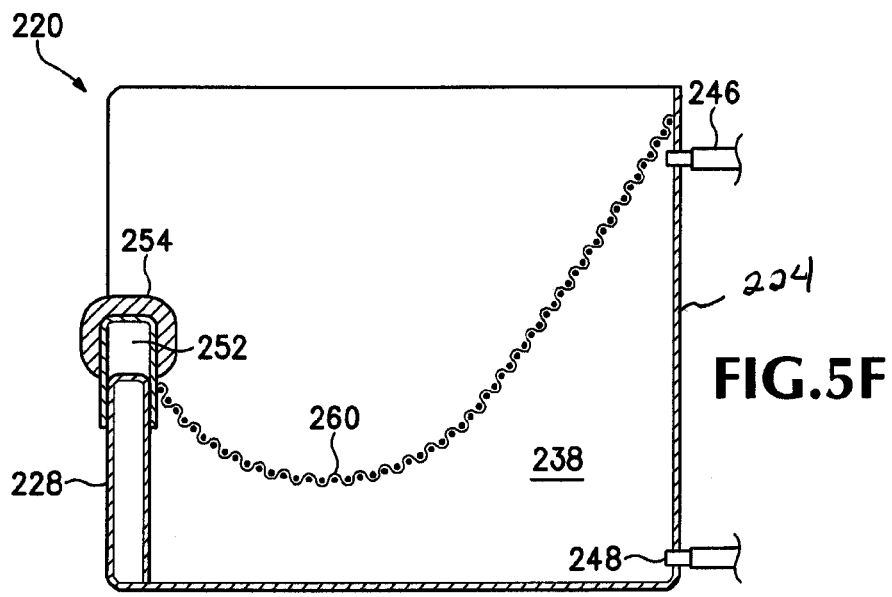
FIG. 5F is yet another embodiment of the head receptacle, in which a mesh net forms the receptacle that supports the head over the reservoir of cooling liquid, and forms a permeable barrier through which the liquid returns from the receptacle to the reservoir.

Yet another embodiment of the box is illustrated in FIG. 5F wherein the box 220 forms the reservoir for holding cold liquid, and the front wall of the box is of a reduced height or has a cut-out portion for receiving the head with the neck supported on cushion 254 of height adjustment member 252. However the head receptacle is formed by a liquid permeable net 260 that covers receptacle 238 for holding the head of the subject during hypothermic treatment. Net 260 is secured along one edge to front wall 228 below the level of padding 254 and along an opposite edge to rear wall 224 at the top of box 220. Net 260 therefore forms a liquid permeable support sling for the head of a subject, so that as liquid flows through then out of the aerodigestive tract, the liquid spills on to and through net 260 to be returned to underlying reservoir 238.

Figure 6A:
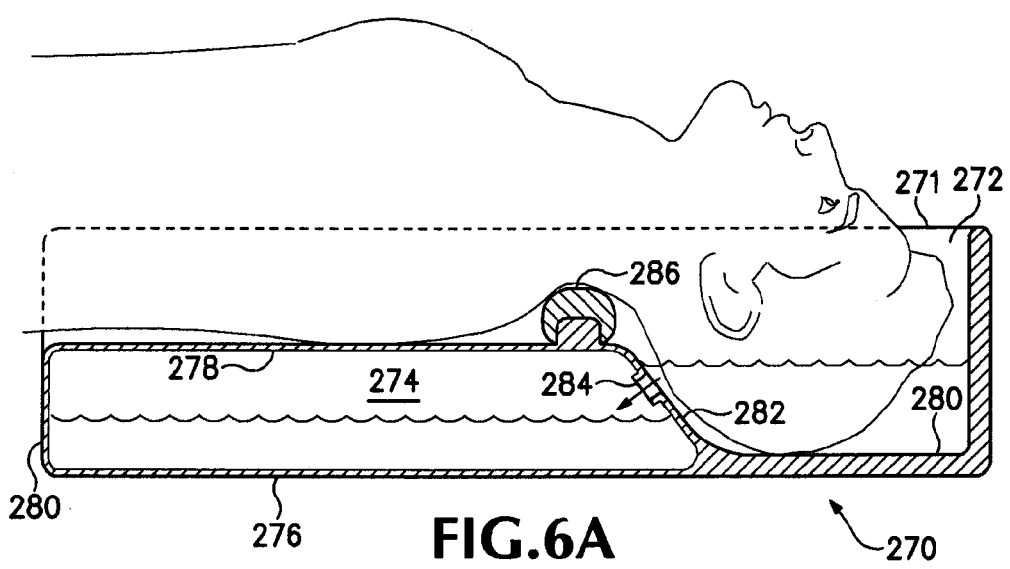
FIG. 6A is a side view showing in cross section a back support and head receptacle, wherein the back support serves as the reservoir of cooling liquid.

In the embodiment of FIG. 6A, the cooling device is in the form of a backboard 270 that contains both a head receptacle 272 and a reservoir 274 for holding a supply of cool liquid. Receptacle 272 and reservoir 274 are in a side-by-side relationship with one another instead of the reservoir surrounding the receptacle as in previously described embodiments. Backboard 270 has a flat rectangular base 276 that is large enough to accommodate upon it the upper portion of a body, for example from the waist or mid-thorax to the top of the head. A top surface of backboard 270 is formed by a flat body support 278 that is spaced from and held parallel to base 276 by opposing sidewalls 271 (only one of which is shown in phantom), an upright bottom wall 280, and an inclined top wall 282 that separates reservoir 274 from receptacle 272. Sidewalls 271 are of the same height as the top of receptacle 272 to thereby also form the sidewalls of receptacle 272.

Inclined wall 282 slopes from body support surface 278 down to bottom surface 280 of receptacle 272. A drain 284 is provided through inclined wall 282 near the junction of wall 282 with support surface 278 to drain liquid from receptacle 272 back into reservoir 274 when the level of liquid in receptacle 272 rises above the level of liquid in reservoir 274, as illustrated by the arrow through drain 284 in FIG. 6A. A cushioned neck support 286 is positioned on body support 278 near inclined wall 282 to protect and assist with the extension of the neck of a subject placed on backboard 270.

In use, a subject is placed face-up on backboard 270 with the neck extended and the head in receptacle 272. The desired irrigation catheters are inserted in the aerodigestive tract of the subject (not shown) and liquid from reservoir 274 is pumped through the catheters into the aerodigestive tract for cooling the patient. The irrigation liquid then flows out of the nose and mouth of the subject and collects in reservoir 272 to be returned to reservoir 274 though drain 284. Backboard support 278 is preferably thermally conductive (for example made of metal) so that the cool liquid in the backboard also cools the body of the subject directly. This direct cooling of the subject's back is particularly advantageous for providing cooling of the spine in patients who may have incurred a spinal cord injury that could benefit from such cooling to reduce inflammation and swelling.

Another embodiment of the backboard cooling device is shown in FIG. 6B, which is similar to the embodiment of FIG. 6A except that body support surface 278' is inclined upwardly to lift the shoulders and neck of the subject. Raising the upper torso in this fashion helps protect the airway and inhibit the entry of liquid into it. It also appropriately positions the head for intubation of the patient and introduction of the irrigation catheters in the aerodigestive tract. The backboard cooling device of FIG. 6B is also shown placed under the back of a patient who is lying face up on a stretcher 288, so that the cooling method can be performed on the subject either in a hospital on en route (for example while in an ambulance or in transit to a hospital).

The embodiment of FIG. 7 illustrates an embodiment of the cooling device that is suitable for treating a subject who has had potential spine injuries and requires stabilization of the spine to avoid additional injury, such as damage to the spinal cord. This embodiment includes a large rectangular tub 290 that is longer and wider than a flat body support board 292 that is suspended above or within tub 290. Support board 292 has lateral extensions that form right and left arm support members 294, 296 and a superior extension that forms a head support 298. In use, tub 290 is filled with liquid 300 that contains sufficient ice 302 to cool it to a desired temperature. Tub 290 therefore provides an underlying large reservoir of cool liquid for introduction through irrigation tubes (not shown) into the aerodigestive tract of a subject placed on support board 292. A patient (not shown) can be positioned supine on support board 292 with the head turned to the side so that internally circulated liquid (and/or any liquid sprayed on the head) can return passively to tube 290 to be cooled there for recirculation to the patient.

Figure 8:
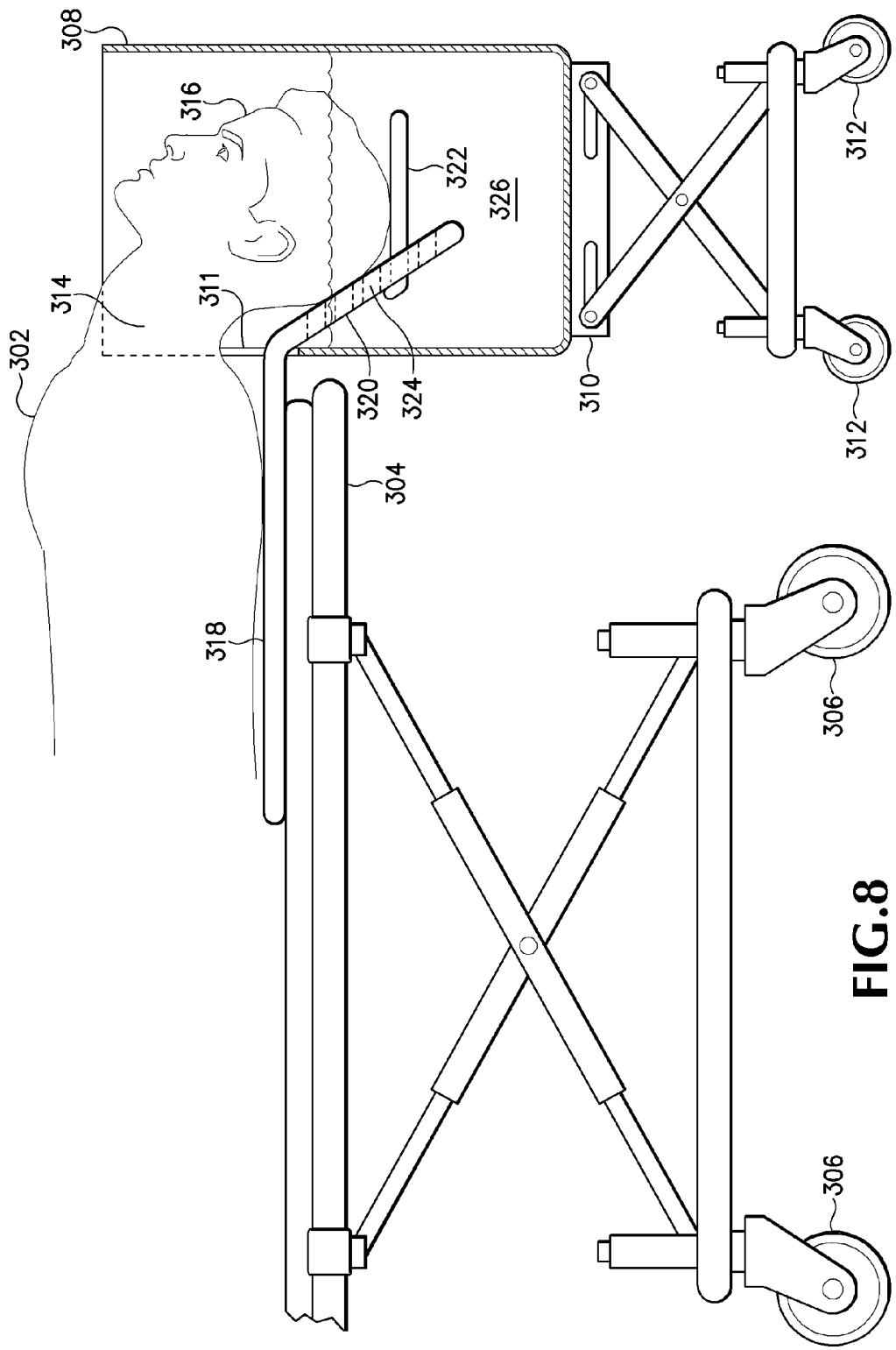
FIG. 8 is a side view of a patient being transported on a stretcher, with a head receptacle that also serves as the cooling liquid reservoir, and the head receptacle moves with the stretcher.

FIG. 8 illustrates a mobile version of the cooling device in which a subject 302 is lying supine on a stretcher 304 that is supported by wheels 306 for transportation of the subject on the stretcher. A separate reservoir 308 is supported on a cart 310 having an adjustable height, and which is also supported on wheels 312 for movement with the stretcher. Reservoir 308 is a large capacity tank that has a cut-out or reduced height portion 311 in which the neck 314 is placed so that the head 316 of the patient can be tilted back and into reservoir 308. A backboard is placed under the back of the patient to support the back and head. The backboard is an angled member that includes several sections: a flat back support 318 for horizontal placement on stretcher 304, an inclined neck support 320 that fits into reservoir 308 through the neck-receiving portion of the reservoir, and a flat head support 322 that is secured to neck support 320 and held substantially parallel to back support 318. Head support 322 mates with a series of ratchets or support grooves 324 on neck support 320 so that the position of head support 322 can be adjusted along neck support 320 while maintaining the substantially parallel relationship between head support 322 and back support 318.

In use, the subject 302 is placed supine on stretcher 304 with back support 318 under the back of the subject, the neck positioned in cut-out portion 311, and head 316 tilted back over the top edge of stretcher 304 with head 316 in reservoir 308 which also serves as the receptacle for holding the head. The position of head support 322 is adjusted to support the crown of head 316 at a desired depth within reservoir 308. Reservoir 308 contains cool liquid 326 up to a level that covers the crown of head 316 to provide external cooling of the head (or below the head if scalp cooling is not desired). As described in connection with other embodiments, irrigation catheters (not shown) are inserted in the subject 302 and cooling liquid 326 is pumped from reservoir 308 into the aerodigestive tract of the subject to achieve the desired rate and degree of cooling. Since both the reservoir and stretcher are on wheels, they are transported in tandem to administer the hypothermia therapy to the subject during transport.

Additional details about the disclosed method and device are provided in the following Examples.

EXAMPLE 1

Temperature of the Liquid

Since permanent brain injury is a major cause of death and disability, more effective methods of brain cooling will benefit a subject's overall medical recovery even if these treatments risk transient damage to other tissue beds. While frostbite can sometimes occur at temperatures less than 0° C., perfluorocarbon (PFC) and other liquids at temperatures used herein are believed to be more beneficial than harmful in this method. For example, household freezers maintain their contents at −17° C. and food (such as ice cream) is consumed at this temperature without damage to the mouth or esophagus. Likewise, cold items from a freezer can be placed on damaged skin to reduce swelling (ice packs to traumatized areas) without unacceptable risk of tissue necrosis.

The esophagus and upper airway are resilient to a variety of damaging stimuli, such as acid reflux, toxic injections, radiation and chemotherapy. The lungs, upper airways and skin have been exposed to 0-4° C. water/saline in cold water drowning without significant sequela. The lung has been infused with large volumes of 4° C. PFC without significant adverse effects, so cold biocompatible liquids that may inadvertently enter the lungs is unlikely to be harmful.

Beneficial results of brain cooling can be seen, for example, with cerebral cooling to approximately 33° C. However, the brain can tolerate much lower temperatures. Animals have had their brains cooled to 10-26° C. and subsequently recovered without significant neurological damage. Humans have been found at 26° C. and subsequently recovered without significant neurological damage. Based on this information, it is believed that the disclosed hypothermic treatment can be used with an acceptable therapeutic risk if the cooled liquid is at a temperature below about 30 or 32° C., and above −20° C., for example above −10 degrees, zero degrees, 10 degrees or 20 degrees. Brief skin and upper airway exposures to liquid with temperature between −30 to −20° C. may also carry an acceptable risk of soft tissue injury. Therapeutic risks of cold damage to soft tissue can also be reduced by inducing the hypothermic cooling at a lower temperature and then gradually increasing the temperature as the risk of soft tissue damage increases and the risk of permanent brain damage decreases.

EXAMPLE 2

Precooling the Brain

The disclosed brain cooling method has been described in connection with the treatment of cardiac arrest, stroke, brain injury and other conditions. However, the method can also be used prophylactically, for example to prepare a patient for cardiovascular surgery in which the patient is placed on a heart-lung bypass machine. Prior studies have shown good outcomes of cardiac surgery performed on humans externally cooled to 25° C. with ice baths. Such patients have had encouraging outcomes after circulatory arrest that lasted for 30 to 77 minutes that was not supported by hear-lung bypass or other means. Adverse neurological outcomes were observed only in 3.8% of surviving patients, predominantly in those with arrest times longer than 30 min The brain cooling method of the present invention can be substituted for the external cooling with ice baths during such procedures.

While "suspending" cerebral metabolism may explain the protective effect of hypothermia, the temperature of the brain at the time that cerebral blood flow is restored may also be an important variable. This hypothesis is consistent with reperfusion-injury theory. Neurological function may be better in patients who have perfusion reinstated after cerebral cooling rather than before cerebral cooling.

EXAMPLE 3

Clinical Indications

A variety of clinical conditions can be treated with the methods and devices disclosed herein. In some embodiments, the method involves determining whether a subject has a condition that would benefit from treatment with the cooling method and then treating the subject with the method once it has been determined that the subject has that condition. In addition, the method includes determining whether the condition would benefit from relatively selective cooling of the brain or non-selective cooling, then administering that type of cooling (or a combination thereof). Examples of such conditions, and a treatment that can be initiated in response to finding that condition, are shown in the following Table 1.

TABLE 1

| Clinical Indications for Cooling, and Types of Cooling |
|---|
| Selective cooling (targets cooling primarily the head and brain) |
|     Anoxic encephalopathy |
|         Cardiac arrest |
|         Hemorrhagic shock |
|         Sepsis |
|     Neonatal anoxic encephalopathy |
|     Stroke |
|         Embolic |
|         Hemorrhagic |
|     Head trauma |
|         Closed |
|         Open |

TABLE 1-continued

Clinical Indications for Cooling, and Types of Cooling

Neurosurgery
    Cerebral aneurism repair
    Hematoma evacuation
    Resection of abnormal tissue or tumor
Cardiovascular surgery
    CABG (Coronary Arterial Bypass Surgery)
    Valve surgery
    CEA (Carotid Endarterectomy)
    Aortic aneurism repair
    Pulmonary arterial embolectomy
High risk general surgery
Procedures with risk of diminished oxygen or blood flow to brain
from
    Hypoxia
    Hypotension
    Systemic or cerebral embolization
    SIRS (systemic inflammatory response syndrome)
Status epilepticus
Fever associated with:
    Systemic infection
    Stroke
    Seizures
    Malignant hyperthermia
    Neuroleptic syndrome
Encephalitis
    Infectious
    Toxic
    Metabolic
Meningitis
Prevention of hospital acquired pneumonia
Non-selective cooling (also targets cooling organs outside of the head)
Early stage of brain cooling
Spinal cord
    Injury
    Ischemia
Myocardial infarction
Cardiogenic shock
SIRS (systemic inflammatory response syndrome)
    Septic shock
    Hemorrhagic shock, large volume transfusion
    Anaphylactic shock
Acute lung injury
    ARDS (adult respiratory distress syndrome)
    Aspiration
    Pneumonia
    TRALI (transfusion related acute lung injury)

Treating Stroke: Many animal studies have shown that cerebral cooling results in improved neurological function and reduced volume of infarct after stroke. Cerebral cooling appears to be beneficial even if initiated hours following the onset of the stroke, however more benefit is obtained if therapeutically effective hypothermia is promptly induced and maintained in accordance with the methods disclosed herein. Cerebral cooling can be used as a primary therapy for stroke, and can also be used as a bridging therapy before attempting cerebral revascularization.

Cerebral revascularization is performed as a standard treatment for embolic strokes. Thrombolytics are routinely used to treat embolic stroke in patients who present to a medical center within 3 hours of initial symptoms. The mechanical removal of cerebral vascular embolism (embolectomy) has been shown to improve neurological function in humans after stroke even if revascularization is delayed until up to 8 hours after the onset of the stroke. Timely revascularization is also combined with the disclosed methods of rapid induction of cerebral cooling to significantly improve neurological outcome after stroke.

Fevers: High fevers are commonly seen in infection, stroke, seizures trauma and adverse drug reactions. Fevers are associated with significantly worse neurological outcomes. Current methods of cooling are often not able to prevent or blunt fevers even when patients are closely monitored in intensive care settings. Fevers often present rapidly (spike) and often last for only 1-2 hours, and current methods of cooling are not able to lower temperatures significantly in this short amount of time even when the brain is normothermic and would be expected to take even longer to cool the brain during fever. The methods disclosed herein are capable of reducing cerebral temperatures to <33° C. in 5-15 minutes even in the face of fever to rapidly blunt fevers and reduce damage to vulnerable organs such as the brain, lungs and kidneys. Rapid interruption of fever spikes is also believed to improve outcomes in systemic inflammatory conditions such as septic shock and acute lung injury.

Surgical Procedures Brain damage is also a risk associated with neurosurgical, cardiovascular and other surgical procedures. Cognitive and behavioral changes are common after CABG (coronary arterial bypass surgery). Episodic hypotension and hypoxia are common occurrences in such high risk surgical procedures. Surgical interruption of cerebral blood flow is also required for cerebral aneurism repair and CEA (carotid endarterectomy) which can induce transient or permanent neurological damage. Cerebral hypothermia is believed to reduce the effects of surgically related brain damage from intraoperative hypotension, hypoxia, interruption of cerebral blood flow (emboli, vascular clamping) or inflammation. Brain cooling before injury results in better outcomes than if cooling is initiated after injury, therefore to prevent or minimize surgery related brain injury cooling is preferably completed before the initiation of surgery, for example between the induction of anesthesia and the beginning of surgery. Cooling can be maintained during surgery and the recovery period.

Myocardial infarction and ischemia: The disclosed rapid induction of therapeutic hypothermia is also believed to be advantageous in subjects who have had a myocardial infarction (MI) whether or not blood flow is reestablished to the affected area. If perfusion is not reestablished, cooling is believed to limit the volume of dead tissue by salvaging the areas with collateral circulation and partial perfusion. Cooling the heart and systemic arterial blood before perfusion is reestablished is believed to decrease reperfusion injury, which may be the primary cause of permanent myocardial damage after MI. In some embodiments of the method, cooling is therefore initiated before revascularization and is continued during and after coronary instrumentation or thrombolysis. Rapidly induced hypothermia cools the heart in a clinically desirable amount of time while reperfusion efforts are underway. Rapid myocardial cooling occurs because cooled blood occupies all four chambers of the heart, cooled systemic arterial blood supplies the myocardium, and the outer surfaces of the heart are directly cooled by the cold liquid in the esophagus and the stomach.

The disclosed cooling methods are safe for use during treatment for acute MI. Cardiac arrhythmias are common after MI and systemic hypothermia increases the risk. It is therefore possible that electrical cardioversion will be required to offset such heart rhythm abnormalities, however cardioversion can be performed safely since the chest and torso will be dry and the device is electrically isolated.

Cooling of the Spinal Cord or Body to Diminish Inflammation: The disclosed method can also be used for non-specific cooling of organs other than the brain. For example, irrigating the oropharyngeal cavities and esophagus with cool water can be used to cool the entire neck or back and adjacent structures, such as the spine and spinal cord (such as the cervical spine) in a trauma victim with a neck or back injury. Such cooling will diminish residual adverse neurological sequelae. Although the spinal cord is thinner than the brain, it is surrounded by more insulating tissue and bone. These insulating features can be overcome, however, by cooling the blood that is perfusing the spinal cord and its surrounding structures. The regioslective features of the disclosed method can be used to enhance treatment of particular types of injuries, or maximize the cooling of specifically affected areas.

Generalized cooling of the spinal cord can be achieved by rapid and significant cooling of the brain, which lowers the temperature of the cerebrospinal fluid (CSF) that circulates around the spinal cord. The introduction of cool liquid through the tubes in the mouth and esophagus will introduce a high volume of turbulent flow against tissues that are very near the brainstem, which can also be helpful in cases of basilar stroke or other injuries to the brainstem. In addition, the cooling of blood returning from the head (for example via the jugular veins) in turn cools the blood in the heart that is subsequently pumped through the aorta and to the vertebral arteries that perfuse the spinal cord. Cooling of the mediastinum by introducing cool liquid into the esophagus and the stomach will cool the blood returning to the heart via the superior and inferior vena cava. This cooled blood will then be pumped to the spinal cord. The overall reduction in body temperature achieved by lowering the temperature of aortic blood also helps reduce the inflammatory response and minimize permanent neurological damage that may otherwise occur to neuron bodies from damage to its neurons.

Although regioselective cooling of the upper aerodigestive tract will target cooling directly to the cervical spine, more generalized cooling can be used to minimize systemic inflammatory effects of trauma to the brain or non-brain structures (such as spinal cord injury or other types of trauma, such as multiple fractures). Complete submersion of the head accompanied by cooling irrigation of the entire aerodigestive tract (but not the lungs) will maximize total body cooling and accelerate induction of protective cooling to minimize the inflammatory response. For example, placement of irrigation tubes into the nasopharynx, oropharynx, and esophagus (and optionally the stomach) will rapidly induce widespread body cooling.

In cases of potential spinal injury, care must of course be taken to stabilize the spine during the induction of rapid brain and/or body cooling. Devices and methods that avoid extension of the neck are preferred in such circumstances.

The disclosed methods cool the spinal cord at all levels relatively rapidly because the cord is thin and of low mass. Cooling of the upper cord is enhanced because it is bathed with cold cerebrospinal fluid (CSF) from the cranium and direct cooling from the upper airway. Cervical spine cooling is targeted for 33° C. within 15-30 or 15-20 minutes of initiating cooling.

Lung cooling: Inflammation associated with lung injury, such as the adult respiratory distress syndrome (ARDS) has been extremely difficult to prevent and treat. Broad anti-inflammatory modulation with steroids has had mixed results and is not recommended for early-stage ARDS. The only targeted anti-inflammatory therapy for sepsis that has come to market is so toxic that it is contraindicated in patient with isolated ARDS and no other organ failure; the morbidity and mortality associated with the drug is greater than that of ARDS alone. In contrast, systemic hypothermia causes less toxicity while demonstrating broad anti-inflammatory properties. Prior studies have shown that cooling in ARDS provides a 33% reduction in predicted mortality when body temperature is reduced to 33° C. in severe ARDS otherwise refractory to non-cooling treatments.

The lungs cool more quickly than most other organs (including the brain) when the non-selective cooling methods disclosed herein are used. The lungs have the greatest ratio of blood flow to organ mass in the body and the full cardiac output runs through them. The lungs are also insulated by air in the airspaces, which compose the majority of the lung's volume, and have a low metabolic rate.

Avoiding Hospital Acquired Pneumonia: Hospital acquired pneumonia, particularly for a patient receiving mechanical ventilation, is caused by translocation of bacteria from the upper airway to the lung. Currently, prevention of ventilator associated pneumonia relies on attempts to disinfect the upper airway using an antibacterial mouth wash applied twice daily in combination with frequent oral care. However, the disclosed cooling is believed to lower the incidence of ventilator associated pneumonia by reducing the number of viable bacteria in the upper airway by washing away bacteria with the large volume of cooling liquid that passes through the upper airway. The temperature of the cooling liquid renders the bacteria inert and can even kill many species. In addition, cooling liquid that contains propylene glycol further reduces the number of viable bacteria because propylene glycol has broad antibacterial properties.

EXAMPLE 4

Inhibiting Flow of Cool Liquid into Lungs

Maintaining the lungs free of the cooling liquid avoids loss of the liquid from the upper airway and helps maintain more effective gas transport in the lungs. A variety of techniques are disclosed as means for inhibiting the entry of the cool liquid into the lungs.

For example, the subject's head and neck may be extended unless contraindicated (for example when cervical spine damage is suspected). Head and neck extension reduces the risk of cold liquid entering the lung by elevating the level of the entrance of the trachea (the larynx) compared to the level of the liquid.

Alternatively, the subject is placed in the Trendelenburg position with the head lower than the chest. This position reduces reduce the risk of cold fluid entering the lung by elevating the level of the entire trachea and lungs compared to the level of the liquid.

Another possibility is to elevate the subject's chest on a firm (possibly padded) board approximately 10 to 30 cm thick. The chest elevation raises the level of the entire trachea and lungs compared to the level of the liquid. In some embodiments the board will have a defect in the midline of the cephalad portion to allow the neck to hyperextend without impingement on the board. The board may also extend under the head at a thickness of 2 to 6 cm, positioned under the box to support the box. The board is firm enough to support CPR.

As shown in the detailed embodiments of the method, a multi-lumen endotracheal tube with an inflatable balloon cuff (or for infants without a cuff) may also function to keep cold liquid from entering the lungs. In some embodiments, the cuff can comprise an ultrathin high volume cuff. The pressure in the cuff can be, in some embodiments, greater than about 30 cm $H_2O$.

The endotracheal tube may also contain a third lumen with the distal opening immediately proximal (above) the inflatable balloon cuff and with the proximal end connected to suction. This third lumen will remove liquid proximal to the balloon cuff, reducing the amount of liquid that would need to be blocked by the balloon cuff.

Active removal of liquid from the pharynx can be provided to further restrict fluid entry into the subject's lungs. For example, tubing under a negative pressure can be provided with an open end or port located in the oropharynx or hypopharynx. In this manner, fluid can be actively removed from the pharynx and returned to the reservoir. The negative pressure in the tubing can be accomplished, for example, by using a suction device such as a suction pump or other such device.

Similarly, active removal of liquid from the trachea can be provided to further restrict fluid entry into the subject's lungs. Such subglottic suction can be achieved via a lumen on a cuff (as described above) positioned in the trachea or by providing an open end or port of a tube in the trachea (e.g., above an endotracheal tube cuff). The tubing can be under negative pressure to pull liquid into the opening or port to remove liquid from the trachea. The removal of fluid from the trachea can be intermittent or continuous. The rate of fluid removal can be monitored to determine the amount of fluid being delivered to the trachea. If the rate is too high measures can be taken to reduce fluid in the trachea, such as increasing the suction pressure, extending the period of use of a suction pump configured to remove fluid from the trachea, and/or decreasing the flow of fluid into the aerodigestive tract (and, in particular, in the area of the trachea).

In other embodiments, a modified laryngeal mask airway (LMA) can be provided to restrict fluid from entering the subject's lungs. The LMA can have an inner diameter greater than an outer diameter of an endotracheal tube (ETT) positioned in the trachea. A portion of the LMA can be removed so that the LMA can slide over an existing ETT. The portion that is removed can be, for example, a portion of the perforated membrane in a central region of the LMA. In use, the LMA circumferential cuff can be inflated so that the circumferential cuff seals the larynx off from the pharynx. In some embodiments, a suction tube can be provided to remove fluid around the mask. If desired, the suction tube can be attached to the mask. Once the LMA is in position, the ETT or other suction tube can be removed from the opening in the LMA, leaving the LMA in place.

EXAMPLE 5

Liquid Flow and Temperature

The total amount of liquid introduced into the cool liquid reservoir can be varied according to the needs of the patient. As already noted, the cool liquid can be introduced at a depth that covers the entire head and face. Another option is to keep the liquid level below the level of the endotracheal balloon. The pump flow (from one or more pumps) can be adjusted to provide overall liquid flow in the range of 0.5 to 50 or 60 L/minute to the internal catheters (not including the catheters provided for directing a turbulent flow of cooling liquid against the scalp of other structure that does not involve insertion of a catheter into the mouth or nose). In certain examples this flow is at least 10 L/min The total flow is typically delivered through 1-6 (such as 2-6) or more catheters. The position of inflow and outflow catheters can be changed over time if needed to provide or maintain liquid flow over the scalp and in the upper airway.

Non-limiting examples of flow rates for particular nasal-oral cooling are 0.5-6 L/min flow in the nose alone. In other examples, the flow rate in the nose can be at least 2 L/min, such as 2-20 L/min. Esophageal flow rates can be independent of other flow rates, and, in some embodiments can be between about 0.5-6 L/min flow in the esophagus alone. In other examples, the flow rate in the esophagus can be at least 5 L/min, such as 5-20 L/min The maximum flow rates selected should not exceed those that are considered are safe and well-tolerated by the patient.

In certain embodiments, flow can be adjusted to be 0.5-10 L/min into the upper airway and 1-20 L/min on the scalp for adults, less for children and infants. A particular reservoir (such as a box in which the head is partially or totally immersed) has a total volume of about 40 liters if the box is about 35 cm on all sides. In such particular embodiments, 5 to 15 or 20 total liters of cold fluid are present in the reservoir, for example about 10 liters. The contents of the reservoir can be circulated about twice a minute, or more, to achieve a desired degree of turbulence that enhances head cooling. To maintain high flow cooling at a low temperature, even larger reservoirs of cooled liquid can be employed, such as reservoirs that contain 20 or more liters (for example at least 30 or 40 liters) of the cooling liquid at the desired temperature (for example, less than 5° C., 0° C., or −5° C.).

To achieve optimal cooling, different flow rates of cooling liquid can be introduced through different catheters that are used in the method. Optimal flow may differ for different tubes, clinical indications and patients but non-limiting examples of flow rates for selected internal tubes include:
  Nose tube(s)—6 L/minute (combined, right+left nasal cavity at 3 L/min each)
  Mouth tube—8 L/min
  Upper esophagus—8 L/min
  Lower esophagus—8 L/min
  Stomach—12 L/min
  Total Flow Rate—42 L/min
An alternative combination of flow rates is illustrated by this example:
  Nose tubes(s)—6 L/min (3 L/min each nostril)
  Oral and esophagus—12 L/min combined (from a single pump)
  Total Flow Rate—18 L/min
  An example of a rate of external flow of cooling liquid against the scalp is 20 L/min In other non-limiting examples, when cooling only the upper airway (all exposed external structures of the aerodigestive tract above the trachea and esophagus), a minimum of 10 L/min total flow can be provided through two nasal catheters and one oral catheter. In an example that also includes irrigating the upper esophagus, lower esophagus and stomach, the total flow can be about 30 L/min In other examples, the flow per catheter can be about 2 L/min For instance, when irrigating above the esophagus with three catheters (one each in nostril and one in the mouth) then the flow above the esophagus can be about 6 L/min (2 nasal and 1 oral catheter). This is a higher flow rate than in prior methods of cooling. Then when adding catheters (or lumens) to introduce cooling liquid at three ports below the entrance to the esophagus (for example, two in the esophagus and one in the stomach) an additional 6 L/min would be introduced into the aerodigestive tract for a total of 12 L/min In other embodiments, because of the cumulative effect of adding multiple irrigating catheters, the flow rates associated with each catheter can be relatively low, such as about 0.5 L/min In another example, if cooling liquid is only introduced into the nose using 2 L/min in each nostril, then the total flow rate of cooling liquid into the aerodigestive tract (in this case the upper airway) is 4 L/min The temperature of the liquid in the container can be adjusted by various cooling means over time, for example by any one or combination of the following methods:

adding cold liquid to the reservoir to increase the volume of liquid in the box removing an aliquot of warmer liquid and replacing it with colder liquid placing inert cold objects within the reservoir placing frozen water (water ice) or CO2 (dry ice) within the reservoir (as used herein, "ice" refers generically to a solid phase of a non-metallic substance that is a liquid or gas at room temperature)

placing a heat exchanger in series with the reservoir and the pump

Additional air may be added to the balloons of the endotracheal tube and the esophageal catheter to compensate for volume loss in the balloon as the air within the balloon is cooled.

The initial temperature of the liquid is in the range of −30 to +30° C. Optimal temperature may vary during treatment but is believed to be in the range of −20 to +10° C.

The ideal cooling liquid is biologically compatible (for example nontoxic) and has a melting point in the range of −50 to +10° C. and a boiling point of greater than 50° C. Examples of liquids meeting these are listed in Example 12. Liquids can be combined or used in series during the treatment.

Although various flow rates are described herein, it should be understood that many of the general advantages of the disclosed embodiments can be achieved using either high or low flow rates. By irrigating various portions of the upper aerodigestive tract (excluding the lungs and intestines), the cold fluid in the aerodigestive tract can extract heat from the perivascular tissue (tissue surrounding the arteries of the head, neck and mediastinum), which in turn extracts heat from the blood in the carotid and vertebral arteries. The cold blood then extracts heat from the brain and returns to the body having been warmed by passage through the brain. This chain of events means that extracting a joule of energy from the patient's brain and into the aerodigestive tract fluid involves several interacting transport processes. Without being bound by theory, it is believed that the convective transfer of heat into the forced flowing cooling fluid in the aerodigestive tract will be much faster than conduction through the perivascular tissue of the patient. As a result, increasing the length and/or area of the cooled region in the manners described herein is particularly helpful to improve cooling of the brain.

As discussed above, in some embodiments, increased flow rates may improve cooling of the brain; however, it should be understood that the systems described herein can function effectively with both high and low flow rates when the free-flowing liquid is introduced to the larger cooling regions as disclosed herein. In addition, by increasing the length and/or areas of cooling as described herein, the regions of cold tissue created around the aerodigestive tract can overlap a greater portion of the key arteries that supply blood to the brain, thereby creating a longer zone for the blood to cool on its way to the brain.

EXAMPLE 6

Multistage Cooling (Induction and Maintenance)

The cooling methods disclosed herein can be used for multi-stage treatments, for example using induction and maintenance regimens. In certain examples, the induction stage can take 15 minutes to an hour, followed by a maintenance phase that can last greater than 12 hours, for example, 12-48 hours, such as up to a week or more. Different issues related to side effects arise during such long duration treatment, for example chemical or thermal toxicity of the liquid caused by sustained exposure to the cooled tissues of the aerodigestive tract. To address these issues, different liquids and temperatures can be used in the induction and maintenance phases of the treatment. For example, lower liquid temperatures will be used in the induction phase to achieve more rapid cooling, while higher liquid temperatures can be used in the maintenance phase. In one example, the temperature of the cooling liquid during the induction phase is −30 to 5° C., while the liquid temperature in the maintenance phase is 5 to 30° C. Liquid flow rates are also varied depending on the stage of treatment. For example, higher flow rates can be used during induction to achieve more rapid cooling, while lower flow rates can be used during maintenance for a more prolonged period of time.

In one example, a liquid temperature below 0° C. is used for the induction phase to achieve more rapid cooling (for example during the first 30 minutes to one hour of cooling). Temperatures below 0° C. are achievable with liquids such as propylene glycol cooled with ice. After cooling induction, higher temperatures (above 0° C.) are used for maintenance. Such temperatures are readily achieved with cooled water.

Given the urgency of cooling the subject quickly to achieve maximal benefit from the procedure, less controlled conditions may be used during rapid induction, for example in the field (such as in an ambulance) before a subject is brought to a hospital. Hence the subject's head may be partially or completely immersed in a container of ice water by emergency medical technicians who have been sent to retrieve a patient who may benefit from the treatment. The liquid in the container can also be used to supply the irrigation fluid for the aerodigestive tract at a less controlled temperature than would be achieved in the more controlled in-patient setting (as in an intensive care unit).

Different body regions can also be cooled in different stages of the treatment. Portions of the head and aerodigestive tract that are suitable for irrigation with turbulent cold liquid include external structures such as the scalp and face, and internal structures of the aerodigestive tract such as the nasopharynx (through nose tubes), the oro-hypopharynx (through a mouth tube), the esophagus (through one or more esophageal tubes), and the stomach (through a stomach tube). During induction, when rapid cooling of the brain and/or body is desired, all regions may be used for cooling unless otherwise contraindicated. Alternatively, during induction catheters can be placed in all these locations except the stomach. During maintenance treatment, any combination of the external and internal structures can be used to achieve desired degrees of targeted or non-targeted cooling.

As discussed above multi-stage cooling can include an initial induction cooling stage and later maintenance cooling stage. In some instances, these stages (or a portion of each stage) can take place at different locations. For example, a subject may begin the induction stage at a first location (e.g., outside of a hospital setting such as in an ambulance, at the place of injury, etc.) and the induction stage can be continued or the maintenance stage begun at a second location (e.g., at a hospital). Accordingly, it can be useful to provide a system wherein various elements (such as the tubing, pump, etc.) are capable of being transferred with the subject from the first location to the second location. At subsequent locations, such elements can be reconnected, if necessary, to systems and cooling fluids provided at the subsequent location.

In one embodiment, the aerodigestive tract and/or upper airway can be cooled while the subject's head is at least partially submerged in a reservoir during an induction stage. Then, during transfer of the subject to the section location, the subject's head can be removed from the reservoir and the cooling of the aerodigestive tract and/or upper airway can be continued without external cooling of the head by submersion in a reservoir. In this case, the cooling liquid can be delivered and recirculated from the original reservoir (from which the subject's head was removed) or, if desired, the cooling liquid can be delivered and recirculated from a different external reservoir.

In another embodiment, the reservoir that supplies the cooling liquid to the aerodigestive tract and/or upper airway can be separate from the reservoir that supplies the cooling liquid that cools the external surface of the subject's head. In this manner, the subject can be readily transitioned from an induction stage in which an external surface of the subject's head is cooled along with the cooling of the aerodigestive tract and/or the upper airway to a maintenance stage where only the aerodigestive tract and/or the upper airway is cooled.

Although multistage cooling is described, it should be understood that the systems and methods described herein can be performed separately. Thus, for example, if desired, the upper airway and/or aerodigestive tract can be cooled without providing any external cooling (e.g., to an external surface of the head).

EXAMPLE 7

Selective and Non-Selective Cooling

The disclosed method and device can be used to preferentially or selectively cool the brain ("selective mode") or to cool the entire body ("non-selective mode").

In the selective mode, the aerodigestive regions to be cooled by applying cooling liquid are only the nasopharynx and oropharynx; in some embodiments the cooling liquid is also introduced into the upper esophagus. Liquid may optionally be inhibited from entering the lower esophagus and the stomach by placing an esophageal balloon that obstructs the lower esophagus. However, in some embodiments of selective cooling the esophagus is not mechanically obstructed.

In non-selective mode, the following regions are cooled: scalp, face, nasopharynx, oropharynx, and portions of the gastrointestinal tract, such as one or more or all of the upper esophagus, lower esophagus, and stomach.

Selective cooling allows for lower temperatures in the brain with less cooling of the body core and therefore less systemic toxicity. In animal models, brain temperatures of 15° C. have been shown to be very well tolerated and therapeutic, while core body temperatures of <30° C. are associated with increased risk of cardiac arrhythmia, pneumonia and electrolyte shifts. Cooling "overshoot" does not appear to have any adverse effects in the brain.

Non-selective cooling is used to reduce the effects of inflammation and ischemia throughout the body. Many diseases or conditions are driven by inflammation: reperfusion injury after organ ischemia, septic shock, trauma and allergic reactions. Cooling has a potent broad non-selective anti-inflammatory effect and is currently being studied as a treatment for some of these conditions.

Cooling outside of the cranium is accomplished by cooling the arterial blood supplying the organs or structures of interest, or the body in general. Experimental data from use of the disclosed device and method have demonstrated significant cooling of the aortic blood, at approximately the same rate and depth as that of the brain, even without cooling the lower esophagus or stomach. Arterial blood temperature (measured in the aorta) is decreased by profoundly cooling the blood returning to the heart from the head and neck. Cooling of the face and scalp cools the blood delivered to the extracranial structures of the head via the external carotid artery. In addition, cooling of the tissue surrounding the upper aerodigestive tract (above the esophagus) also adds to the coolness of the returning jugular venous blood. Cooling of every possible surface of the head and the entire upper airway provides effective non-selective cooling.

Cooling structures below the upper aerodigestive tract, such as the lower esophagus and stomach, increases the rate of systemic arterial blood cooling. Cooling of the entire mediastinum can be achieved by cooling the full length of the esophagus as well as the stomach. The proximity of the esophagus to the superior vena cava, right atrium and inferior vena cava allows for cooling of blood coming from all areas of the body. Therefore, cooling of the entire esophagus and the stomach allows for more rapid cooling of systemic arterial blood by cooling all venous blood as it returns to the heart.

Although some currently available hypothermia devices rely on non-selective cooling, they are unable to provide non-selective cooling at therapeutically beneficial rates. The methods and devices disclosed herein are optimally able to achieve a therapeutic target temperature in the brain within 5-10 minutes, but optimal cooling of most of the non-brain organs is expected to require more time. The rate and depth of cooling of an organ will depend on multiple factors, including the organ's mass, metabolic activity, rate of blood flow and cold induced vasoconstriction in addition to the temperature of the blood perfusing the organ. This amount of time is still much less than that required by state-of-the-art devices, which require 3-6 hours.

The methods and devices disclosed herein are also capable of delivering a rapid "burst" of hypothermia to affected organs (such as the brain) early in the course of treatment. Rapid induction of hypothermia allows for a more definitive reduction of inflammation at the beginning of the inflammatory cascade, which is believed to significantly enhance the effectiveness of treatment. Early temperatures in target organs could briefly be obtained that are far lower than what would be considered toxic if maintained throughout the body for a prolonged period of time.

Any "overshoot" of systemic cooling can be rapidly corrected. Since continuation of cooling requires continued use of the device, merely discontinuing or diminishing treatment will result in an increase in body temperature. This rapid reversibility contrasts to other state-of-the-art devices which require warming of the entire mass of the body if the core body temperature decreases to an unwanted level. Warming the entire mass of the body is a slow process.

In certain embodiments of the method, therapeutic hypothermia is induced non-selectively followed by selective cooling (for example of the brain to result in very rapid cooling of the brain). Delivery of warm blood from the body via the carotid and vertebral arteries normally counteracts cerebral cooling. However non-selective cooling results in a rapid decrease in systemic arterial blood temperature, resulting in cooler blood entering the carotid and vertebral circulations in the upper chest and allowing for an even lower temperature of blood as it enters the brain. Non-selective cooling also decreases the minimum plateau temperature achieved in the brain. The minimum temperature of the brain is a balance between the amount of heat delivered to the head from the body and the amount of cold delivered by the device. Since non-selective cooling decreases systemic arterial blood temperature, less heat is delivered to the head and lower brain temperatures are possible, and are more rapidly achieved.

After the brain has reached its goal temperature (predicted by non-invasive measurements) cooling can be switched from non-selective cooling to selective head cooling. This change helps avoid adverse reactions from body core hypothermia. After selective cooling is initiated, body warming can be initiated to slow or reverse the temperature decline for the body core.

EXAMPLE 8

Emergency Cooling with Rapid Induction

An advantage of the disclosed methods and devices is that they are capable of inducing rapid cooling of the brain and/or other organs and/or the entire body. Such rapid cooling has been found particularly beneficial in the avoidance of permanent tissue damage and the promotion of full functional recovery. Certain embodiments of the invention are therefore designed for use by emergency medical technicians in the field, for example in ambulances transporting patients to a hospital.

A cooling unit (such as a small freezer) may be placed in an ambulance, and the unit contains 5-50 liters of a cooling liquid (such as 20% propylene glycol in water). If the technicians find a subject who has a condition that would benefit from brain and or body cooling (as detailed in other sections of this specification), then rapid field-induction of brain or body cooling can be achieved by quickly immersing the head of the patient in cooling liquid. To simplify use of the device in the field, ice can be placed in the liquid to maintain it at the desired temperature. The iced liquid in which the head is submerged also serves as a reservoir of cooling liquid that can be directed in a turbulent flow externally against the head, and/or used as an irrigating fluid for introduction into the aerodigestive tract. This simple version of the device will not require any electrical cooling devices, and cooling can be maintained by ice cooled liquid alone for the duration of transportation of the patient to the hospital.

When used in the field, and to simplify the technique for rapid induction and ease of transportation, the cooling of the aerodigestive tract may be carried out without external application of cooling liquid to the head, as would occur in partial or total immersion of the head. However, the cooling liquid may optionally be applied externally to the head to further accelerate rapidity of therapeutic hypothermic induction.

EXAMPLE 9

Pump Embodiments

Although only one pump is shown in FIG. 3 to drive liquid externally over the head and internally through the upper airway, multiple pumps can instead be incorporated into the system. For example a first pump would draw liquid 118 from the reservoir in container 112 through a first inlet conduit to the first pump and pump the liquid back through a first return conduit into container 112 externally over the head. A second pump would draw liquid from the same reservoir through a second inlet conduit to a second pump and pump the liquid back through a second return conduit to the upper airway catheters. An advantage of the separate pumps is that the flow of liquid can be separately regulated for external delivery around the head and internal delivery into the upper airway. This is a particular advantage when the caliber of the upper airway catheters is different than the conduit for external delivery of the liquid, and the internal resistance of the external and internal delivery systems differs.

In other embodiments of the method that use multiple catheters, each catheter can be associated with a separate pump. Alternatively, a separate pump can provide liquid flow to all catheters in a particular anatomic regions, such as all the external catheters, all the internal catheters, all the catheters in the upper airway, all the catheters in the gastrointestinal tract (esophagus and/or stomach), etc.

The pump or pumps may be either manually operated or non-manually powered, for example by electricity. A hand or foot powered pump is particularly useful for field operation outside a hospital or ambulance where a source of electricity may not be readily available. Once the patient is transported to an ambulance or hospital, the pump can be connected to a source of electrical energy and automated pumping initiated and continued for a sustained period of time. Batteries can also be used to power the pump for field operation.

The pump or pumps can include one or more filter mechanisms to remove any undesirable materials from the liquid as it is circulated out of the subject. Such undesirable materials can include, for example, microbes or other loose matter present in the area of the body where the cooling liquid is introduced. Such undesirable materials can be picked up and carried out of the body as the cooling liquid is discharged from the body. The filter mechanism can remove such materials from the cooling liquid and the pump can reintroduce the filtered cooling liquid into the body. As described in more detail in Example 12 below, by filtering the circulated cooling liquid in this manner, the cooling liquid can help sanitize the treated portions of the subject (e.g., the upper airway and/or aerodigestive tract).

EXAMPLE 10

Esophageal tubes

A variety of specialized multi-lumen esophageal tubes can be provided to deliver the high flow of cooling liquid to the aerodigestive tract in those embodiments that employ esophageal irrigation. For example, a double or triple coaxial tube may be employed.

In the triple coaxial tube, the inner lumen is the longest and acts as a nasogastric tube hooked up to suction, for example to remove cooling and other liquids from the stomach if desired. Alternatively, the long inner lumen can be used to deliver cooling liquid to the stomach. The middle lumen delivers cooling liquid and may have multiple side ports for omni-directional delivery of the cooling liquids in multiple different directions and at different levels of the esophagus. The outer lumen can selectively remove cooling liquid from the esophagus if desired. However, lamellar flow of returning liquid moving along the wall of the esophagus toward the mouth is helpful in achieving heat transfer to the liquid, hence suctioning of return liquid is not normally used absent special circumstances.

Alternatively, multiple parallel tubes of different lengths are used to introduce flow into the esophagus. The longest tube is positioned with its tip in the stomach, and may serve to either introduce cooling liquid or suction cooling liquid from the stomach. This tube has an inflatable balloon around the tube about 10 cm from the distal end of the tube. The balloon can selectively be inflated in the distal esophagus if it is desired to isolate the stomach from the flow of liquid in the esophagus so that the cooling liquid is directed more selectively to the esophagus. The mid-length tube is of a sufficient length to be positioned with its tip about 3 cm proximal to the balloon on the first tube; the mid-length tube has multiple side ports for the delivery of the cooling liquid. The short tube is positioned with its tip in the hypopharynx; this tube has multiple side ports along its length for about 5 cm for omnidirectional delivery or removal of cooling liquid in the hypopharynx.

EXAMPLE 11

Mouth and/or Nose Drainage

An advantage of certain embodiments of the device and method is that the cooling liquid is capable of draining passively through the mouth and/or nose without application of suction. Removal of liquid through the mouth and/or nose avoids removal through suction tubes placed in the aerodigestive tract, and therefore provides flow of the cool return liquid over the large surface area of the tissues of the aerodigestive tract to maximize heat exchange between the tissues and the liquid. Drainage of the liquid through the mouth and/or nose can be achieved with the head entirely submerged in the cooling liquid, partially submerged in it, or not submerged at all.

In some illustrated embodiments, liquid that drains out of the mouth collects in a reservoir around the head. However, the draining liquid can also collect in a reservoir that is below or beside the head. For example, the head may be supported by a permeable support surface having an opening or openings through which liquid returns to the reservoir. The draining liquid can then be cooled and returned to the aerodigestive tract for continued cooling of the tissues.

In one example, the head may be turned to the side so that liquid will pour out one side of mouth, which will help avoid contacting the cool liquid with the face and help keep liquid out of the lungs by lowering the level of liquid in the upper airway. The head can be gently restrained to keep the head turned to its side, and the corner of the mouth may be pulled down to encourage egress of liquid from the mouth. In some embodiments a drainage tube can be place in the mouth to further reduce the level of liquid in the mouth.

If desirable, oral and/or nasal barriers can be provided to restrict or prevent the exit of cooling fluid from the subject's body (e.g., from the upper airway and/or aerodigestive tract). Such barriers can be useful for keeping the field (e.g., the head, bed, etc.) dry during long-term use of the devices disclosed herein.

Nasal plugging can ensure that returning fluid exit the body via the mouth and can comprise, for example, partial or full rings made of a soft shape-holding material that can wrap around any tubes that are inserted in the nose. Each ring can fit tightly around the tubing and also fit tightly along the mucus membrane of the interior surface of the nares. The rings can be supplied separately from the nasal tubing for attachment by a user.

Alternatively, such rings can be manufactured or sold in a condition where they are already attached to nasal cooling tube(s). In some embodiments, the ring or other such plugging member can be fixed relative to the nasal cooling tube(s) to ensure that the tip of the nasal cooling tube is not inserted too far into the pharynx. Such rings can also help to keep the tubing in proper placement during an operation and/or any situation where the position or location of the subject's body may be altered or adjusted.

Oral barriers can comprise semi-permeable or solid, soft, shape-holding substances that are placed between the teeth/gums and the lips/buccal mucosa. This bather can prevent cooling fluid from leaving the mouth at undesired locations. For example, if a mouth gutter is being used on one side of the mouth, the oral barrier can be placed on the opposite side of the mouth to direct fluid flow towards the gutter. In another example, the entire mouth could be covered with the oral barrier. In such a case, defects within the barrier can permit some fluid to escape there-through and/or can permit a tube to be placed through the barrier at those areas.

The oral barriers described herein can be rigid or pliable. A pliable barrier can allow for bulging which would indicate higher fluid pressures in the upper airway and could be used as an indicator to the user of the pressure of the fluid in the airway. The barrier can extend into the mouth in multiple directions to ensure that, when pressure increases and the diameter of the oral opening increases, the barrier remains generally in place and does not allow fluid to pass between the barrier and the lips.

In some embodiments, the bather can be connected to a mouth gutter (or funnel) type device to allow for drainage of the fluid from the mouth. The gutter or funnel can be open to the air or sealed tightly with the oral barrier.

EXAMPLE 12

Cooling Liquids

A variety of biologically compatible cooling liquids can be used, either alone or in combination, in the disclosed methods and devices. A biologically compatible liquid is one that is either non-toxic, or that has levels of toxicity that are acceptable in view of the problem being treated. Some toxicities are minor (such as skin irritation that can be caused by glycerol), and others are more significant (such as causing electrolyte abnormalities) but can be medically managed. As long as the toxicity presented by use of the liquid is acceptable in the clinical circumstances in which it is used, the liquid is biologically compatible. Any liquid that causes a severe permanent injury or is incompatible with life is not considered biologically compatible. Liquids that may not be biologically compatible at high concentrations can in some instances be made biologically compatible by adding a diluent (such as water).

Examples of biologically compatible liquids are listed in Table 2.

Cooling liquids particularly useful in the methods disclosed herein have high heat transferability. Gases are not suitable for this purpose because they do not transfer heat at the rate envisioned by the disclosed methods. The optimal temperature for a particular liquid is often the lowest temperature that can be achieved without freezing, and with an acceptable degree of viscosity. Since liquids usually become more viscous as they are cooled, there is an optimal balance of temperature and viscosity. For example, the liquid is cooled until it reaches a viscosity of 5 to 10 times the viscosity of water at 0° C.

Colder cooling liquids increase the rate of brain and/or body cooling, however the rate of cooling is balanced with the potential tissue damaging effect of the cold liquid. However, animal (including human) tissue can tolerate surprisingly low temperatures, at least for limited periods of time. Items from food freezers (−17° C.) are routinely placed on skin after trauma to reduce swelling, which illustrates the ability of skin to tolerate such low temperatures. The mucous membranes (such as those found in the aerodigestive tract) also tolerate low temperatures, as illustrated by the fact that items from food freezers (−17° C.) are routinely eaten.

Mixtures of liquids are particularly contemplated as useful in the disclosed methods. For example, mixtures that take advantage of interactions with water can be used. A water/propylene glycol mixture is a preferred liquid for induction because it can be cooled to temperatures below 0° C. A water/saline cooling liquid will likely be used as maintenance liquid to maintain a temperature above 0° C. for 12-48 hours because of its low toxicity. Saline solution has a lowered freezing point, and is easily washed off the patient, staff and equipment.

Examples of cooling liquids include those shown in Table 2.

TABLE 2

Cooling Liquids

Water-based
    Propylene glycol (5-25% in water)
    Ethanol (5-25% in water)
    Glycerol/glycerine (5-25% in water)
    Dextrose (5-25% in water)
    Glucose (5-25% in water)
    Sucrose (5-25% in water)
    Sodium chloride (0.45-5% in water)
    Calcium chloride (1-25% in water)
    Sodium bicarbonate (0.45-5% in water)
Oils
    High-oleic safflower oil
    Corn oil
    Castor oil
Perfluorocarbons
    Perfluorohexane
    Perfluoroheptane
    Perfluorooctane
Additives (optional)
    Detergents (trace)

Trace quantities of detergents such as sodium laurel sulfate, sodium laureth sulfate, etc can be added to the cooling liquid to solubilize debris and bodily fluids (blood, mucus, hair, sweat) and inhibit pump/tubing obstructions.

As mentioned above, a particularly preferred cooling liquid for the induction phase is propylene glycol (PG). The PG is cooled to −10 to −20° C., and is used during induction for 30-60 minutes. This temperature is achievable because PG 40% in water has freezing point of −22° C. PG is in an FDA classification of "generally recognized as safe" and has very low ingestion toxicity. For example, PG is found in high concentrations in foods and cosmetics; the average adult in the United States consumes 2.5 grams/day of PG in food. PG is a common ingredient in mouthwash, and is the main ingredient in many oral and intravenous medications. It causes minimal skin and eye irritation, and is used in many topical medications and personal care products. PG has been nebulized and inhaled for treatment of chronic lung disease. It is easily flushed off mucous membranes and skin by water or saline, so this induction liquid can easily be removed by flushing with saline, water of other liquid that is used in a subsequent maintenance phase of treatment.

Other characteristics of PG that make it very suitable as a cooling liquid are its high specific heat (which is close to water and better than ethylene glycol), a viscosity only slightly higher than water, a surface tension lower than water (when mixed with water), compatibility with many types of flexible tubing and pumps, very low flammability, and no special disposal needs.

A particularly suitable cooling liquid for maintenance of hypothermia is saline solution, such as 0.9% saline solution. An optimal temperature range for maintenance liquid is +5 to +20° C., and an example of a maintenance period would be 12-48 hours. Use of saline maintenance solution for this sustained period of time is particularly suitable because it is considered a "physiologic" fluid. Saline solution during maintenance therapy also avoids dermal and enteral absorption of propylene glycol during long-term use.

Glycerol is a particularly useful cooling liquid component, because when added to water it has a low surface tension. Salt in water (saline solution) has no effect on viscosity and does not decrease surface tension. Sugar solution increase viscosity of the liquid, while ethanol decreases surface tension (but must be treated with caution because of its flammability). Calcium chloride slightly increases the viscosity of a solution, and it used in low concentrations because it can be an irritant at very high concentrations.

The cooling liquids described herein can also function to at least partially sanitize the areas of the body into which they are introduced, including, for example, upper airway and/or aerodigestive tract. Sanitization of the upper airway and/or aerodigestive tract can be useful to reduce the incidence of some complications that are associated with intubation and/or ventilator support. For example, patients who are intubated and receiving mechanical ventilatory support can suffer from ventilator associated pneumonia (VAP). VAP is a relatively common complication that can extend the number of days on the ventilator, the length of stay in the ICU, and increase the risk of death of the patient. The incidence of VAP can, in some cases, be reduced by utilizing or providing various methods described herein including, for example, specialized endotracheal tube (ETT) cuffs, subglottic suction above the ETT cuff, an upright posture and partial sterilization (sanitizing) of the aerodigestive tract using antimicrobial solutions applied to the mouth. Such methods can be supplemented and/or replaced by the utilization of the sanitizing fluids and methods described herein.

The methods and cooling liquids described herein can sanitize the various areas of the body into which they are introduced (e.g., the upper airways and/or aerodigestive tract) in one or more of the following ways. Mechanical sanitization of these areas can be achieved by debridement of microbes from these areas, sheer forces achieved by the flowing fluid, and by removing superstructures or biofilms that can enhance microbe viability in these areas. The sheer forces introduced by the free-flowing cooling liquid as that liquid travels in the body and through the pump and filter systems can further physically stress microbes, thereby killing them and/or reducing their pathogenicity.

In addition, the large volume of cooling liquid can dilute the bacterial concentrations in the areas in the body into which the cooling liquid is introduced, which can further reduce the pathogenicity of surviving microbes. Similarly, by removing, reducing, and/or diluting the nutrients available to the microbes (such as those present in the mucosa), the number and pathogenicity of microbes can be even further reduced by the introduction of the cooling liquids disclosed herein.

Accordingly, the exchange and circulation of cooling liquid can remove mucus, biofilms, and bacterial superstructures mechanically, essentially washing them out of the aerodigestive tract. Once they are removed from the aerodigestive tract (or other areas) and are suspended in the cold fluid they can be removed from the fluid by filtering as described above. Even if not removed by filtering, however, such microbes will be greatly diluted in the reservoir of cooling fluid.

The temperature of the cooling liquids can also play a role since the temperature is preferably sufficiently low to kill microbes and/or otherwise reduced the energy stores and/or pathogenicity of the microbes. Also, microbe adaption to "cold-shock" can take time (e.g., hours) and generally requires large energy expenditures by the microbes. Accordingly, by removing or damaging microbes by filtering them out the body within minutes, the systems and methods described herein can kill or damage microbes before they have time to adjust to the cooler temperature.

The cooling liquid can also include biochemical agents that can further stress, kill, and/or reduce the pathogenicity of microbes in the body. For example, hypertonic or hypotonic fluid, pH adjustments to the cooling liquid, detergents, and/or antibiotics can be provided in the cooling liquid to further damage and/or disrupt microbe function. Examples of antimicrobials that can be included in the cooling fluid are Tobramycin (currently used in eye drops and nebulized lung treatment), Nystatin (currently used in oral rinses), and Chlorhexadine (currently used in oral treatments for patients on ventilators).

The addition of detergents can increase the rate and proportion of microbe death and/or reduced pathogenicity by causing additional damage to the cell membrane while under the stresses of cold, depleted energy reserves and sheer forces described above.

The addition of salts and/or sugars can also have an additional microbe effect, including, for example, killing and decreasing pathogenicity. Salts and sugars that can be included in the cooling liquid include, for example, sodium chloride (e.g., preferably about 0.45-15% by weight in a water-based solution, and more preferably about 0.45-5%), sodium bicarbonate (e.g., preferably about 0.45-15% by weight in a water-based solution, and more preferably about 0.45-5%), calcium chloride, propylene glycol (PG) (e.g., preferably about 1-50% by weight in a water-based solution, and more preferably about 5-25%), dextrose (e.g., preferably about 1-50% by weight in a water-based solution, and more preferably about 5-25%), glucose (e.g., preferably about 1-50% by weight in a water-based solution, and more preferably about 5-25%), sucrose (e.g., preferably about 1-50% by weight in a water-based solution, and more preferably about 5-25%), and glycerin (e.g., preferably about 1-50% by weight in a water-based solution, and more preferably about 5-25%).

Accordingly, the risk of pneumonia or other complications associated with microbes or other elements entering into the lungs can be lessened by the reduction of microbes by the cooling liquid as described herein. By this reduction of microbes, even if the patient were to aspirate any cooling liquid into the lungs, the amount and/or pathogenicity of the microbes will not likely exceed an infective threshold.

Comparative Data

Comparative studies have been performed to compare cooling induced by the method as described by Brown et al., Profound Selective Cerebral Hypothermia in Dogs by Naso-Oral Perfusion and Head Immersion, Surgical Forum 15:413-415, 1964 (Example 14); improved cooling with liquid at 0° C. and scalp, nasal, oral and upper esophageal cooling (Example 15); cooling liquid at −15° C. using scalp nasal and oral cooling (Example 16).

EXAMPLE 13

Surgical Preparation of the Animal

A 98 kg adult female sheep was maintained under surgical plane anesthesia until euthanized. The sheep was subjected to 3 methods of cerebral hypothermia and outcome was measured by the rate and magnitude of cooling of the superficial cortex of the brain and of the systemic arterial blood. Temperatures were recorded every minute in superficial cerebral cortex, in arterial blood in the abdominal aorta, in the pericarotid tissue of the neck, in the rectum (core temperature), and in the device reservoir. Monitoring was performed by continuous ECG, continuous pulse oxymetry, continuous arterial blood pressure, and continuous end-tidal CO2.

During surgical preparation, the sheep was intubated orally with a standard cuffed endotracheal tube (ETT) and mechanically ventilated with 100% oxygen and minute ventilation titrated to an end-tidal CO2 of 35 Ton. Tracheostomy was performed and a cuffed tube was placed with the tip in the lower trachea. Esophagostomy was performed and a cuffed tube was placed with the tip in the mid esophagus and the proximal end to gravity. Arterial and venous catheters were placed in the right groin.

The left mid neck was dissected, a temperature probe was placed lateral to the carotid artery and the site closed at the levels of the fascia and the skin. The scalp was dissected in the left upper parietal region, and a 10 mm bun hole was created through 22 mm of skull. The dura and superficial brain were incised and a temperature probe was placed with tip 7 mm below the surface of the cerebral cortex. The bun hole was sealed with dental cement. The site was closed at the levels of the fascia and the skin and covered with petroleum jelly.

Catheters were obtained for use in the following examples. The catheters had the following inner diameter (ID) and outer diameter (OD):

intake tubes—from reservoir to each of the 3 pumps

ID=½ inch

OD=¾ inch scalp tubes

ID=½ inch

OD=¾ inch nasal and oral and esophageal tubes

ID=5/16 inch

OD=7/16 inch

EXAMPLE 14 (TRIAL 1)

Selective Cooling with Low Flow Cooling Liquid from Catheters Inserted Only Into Nostrils (Brown et al. Method)

One tube was placed in each nasal cavity by inserting the tip of the tube 5 cm beyond each nares.

A box open at the top acted as a reservoir for cooling liquid. The reservoir was filled with water with ice at 0° C. A pump withdrew liquid from the reservoir at 1.8 L/min, introduced it through the tubes into the nasal cavities. The liquid returned passively back to the reservoir via the nose and mouth. At the start of cooling the head was submerged in the reservoir by tilting the surgical table head-down, removing the headrest from the table and extending the neck. At the same time the nasal tubes were connected to the outflow tube of the pump. Cooling was discontinued after 30 minutes, the pump stopped, the head removed from the reservoir and the sheep rewarmed using a warm saline IV infusion and external warming of the trunk. Nasal tubes were left in place and disconnected from the pump.

Cooling was performed for 31 minutes, then rewarming was initiated. The data that was obtained is shown in Table 3.

TABLE 3

Selective Cooling with Low Flow Cooling
Liquid only into Nasopharynx

| | Temperature (deg C.) | | | | |
|---|---|---|---|---|---|
| Time (min) | Brain | Peri-carotid | Aorta | Bath | Core |
| 0 | 38.1 | 37.8 | 37.7 | 1.3 | 38.1 |
| 1 | 38.1 | 37.8 | 37.6 | 1.2 | 38.1 |
| 2 | 37.8 | 37.7 | 37.1 | 1.5 | 38.1 |
| 3 | 37.4 | 37.7 | 36.8 | 1.7 | 38 |
| 4 | 37.1 | 37.7 | 36.6 | 2.1 | 37.9 |
| 5 | 36.7 | 37.4 | 36.3 | 2.2 | 37.8 |
| 6 | 36.3 | 37.4 | 36.2 | 2.5 | 37.8 |
| 7 | 35.9 | 37.1 | 35.9 | 2.5 | 37.7 |
| 8 | 35.9 | 36.8 | 35.9 | 2.7 | 37.5 |
| 9 | 35.9 | 36.8 | 35.4 | 2.8 | 37.4 |
| 10 | 35.6 | 36.5 | 35.3 | 2.9 | 37.3 |
| 11 | 35.3 | 36.4 | 35.3 | 3 | 37.2 |
| 12 | 35.3 | 36.2 | 35.3 | 3.1 | 37.1 |
| 13 | 35 | 36.2 | 35.4 | 3.2 | 37.1 |
| 14 | 35 | 35.9 | 35.4 | 3.2 | 37.1 |
| 15 | 34.8 | 35.9 | 35.3 | 3.4 | 37 |
| 16 | 34.8 | 35.9 | 35.1 | 3.4 | 36.9 |
| 17 | 34.8 | 35.7 | 35 | 3.7 | 36.8 |
| 18 | 34.6 | 35.7 | 34.5 | 3.7 | 36.8 |
| 19 | 34.3 | 35.4 | 34.5 | 3.7 | 36.6 |
| 20 | 34.3 | 35.4 | 34.7 | 3.8 | 36.5 |
| 21 | 33.9 | 35.4 | 34.7 | 3.9 | 36.5 |
| 22 | 33.9 | 35.3 | 34.6 | 4 | 36.4 |
| 23 | 33.9 | 35.3 | 34.1 | 4.2 | 36.4 |
| 24 | 33.9 | 35.1 | 34.1 | 4.2 | 36.3 |
| 25 | 33.9 | 35.1 | 34.1 | 4.4 | 36.2 |
| 26 | 33.7 | 35.1 | 34.1 | 4.5 | 36.1 |
| 27 | 33.4 | 34.9 | 34 | 4.5 | 36 |
| 28 | 33.4 | 34.9 | 34.1 | 4.7 | 35.9 |
| 29 | 33.4 | 34.7 | 34.1 | 4.8 | 35.8 |
| 30 | 33.4 | 34.7 | 34.2 | 4.8 | 35.8 |

EXAMPLE 15 (TRIAL 2)

Selective Brain Cooling

After rewarming the animal from the trial described in Example 14, an oral tube was placed with the tip at the base of the tongue and an esophageal tube was placed with the tip in the upper esophagus. Two additional tubes were placed in the liquid reservoir. When the head was submerged in the reservoir their tips were 4 cm from and pointed towards the right and left parietal scalp. A box open at the top acted as a reservoir for cooling liquid. The reservoir was filled with water with ice at 0° C. At the start of cooling the head was submerged by tilting the surgical table head-down, removing the headrest from the table and extending the neck. Three pumps (1, 2, and 3) were used. The two nasal tubes were connected to the outflow tube of pump 1, oral tube to pump 2, esophageal tube to pump 2 and the two scalp tubes to pump 3. Pumps withdrew cool liquid from the reservoir at 6 L/min for pump 1, and 12 L/min each for pumps 2 and 3. Cooling was discontinued after 21 minutes, the pumps stopped, the head removed from the reservoir and the sheep rewarmed using a warm saline IV infusion and external warming of the trunk.

Data obtained from the method is shown in Table 4.

TABLE 4

Selective Brain Cooling

| | Temperature (deg C.) | | | | |
|---|---|---|---|---|---|
| Time (min) | Brain | Peri-carotid | Aorta | Bath | Core |
| 0 | 36.8 | 36.4 | 35.5 | 1.2 | 36.2 |
| 1 | 35.8 | 36.4 | 35.6 | 1.3 | 36.2 |
| 2 | | | | | |
| 3 | | | | | |
| 4 | 35.9 | 27.2 | 34.1 | 3.4 | 36 |
| 5 | 35.5 | 24 | 33.7 | 3.8 | 35.9 |
| 6 | 34.8 | 21.9 | 33.2 | 3.9 | 35.7 |
| 7 | 34.4 | 20.7 | 32.8 | 3.9 | 35.5 |
| 8 | 33.6 | 19.8 | 32.5 | 4 | 35.3 |
| 9 | 33.3 | 21.1 | 32.4 | 4.2 | 35.2 |
| 10 | 32.9 | 22 | 32.2 | 4.6 | 35 |
| 11 | 32.3 | 21.2 | 31.9 | 4.8 | 34.8 |
| 12 | 32 | 20.2 | 31.6 | 5 | 34.7 |
| 13 | 31.7 | 19.7 | 31.3 | 5.3 | 34.5 |
| 14 | 31.1 | 19.3 | 31.1 | 5.6 | 34.3 |
| 15 | 31.3 | 19.3 | 30.9 | 5.7 | 34.1 |
| 16 | 30.9 | 18.9 | 30.7 | 5.9 | 33.9 |
| 17 | | | | | |
| 18 | | | | | |
| 19 | 30.3 | 22.3 | 30.5 | 6.7 | 33.5 |
| 20 | 30 | 20.1 | 30.4 | 7.1 | 33.3 |
| 21 | 30 | 19.6 | 30.2 | 7.3 | 33.2 |

EXAMPLE 16 (TRIAL 3)

Propylene Glycol as Cooling Liquid (Trial 3)

Continued Cooling after Animal Euthanized (Trial 4)

After rewarming the animal from Trial 2 (Example 15), the esophageal tube was withdrawn and replaced with a second oral tube, so that there were two oral tubes both having their tips positioned at the base of the tongue. Both nasal and both scalp tubes remained in place. A box open at the top acted as a reservoir for cooling liquid. The reservoir was filled with a 1:1 mixture of propylene glycol and water at −15° C. Pumps withdrew fluid from the reservoir at 1 L/min for pump 1, and 3 L/min for pump 2 and 5 L/min for pump 3 for a total of 9 L/min through the internally placed catheters. At the start of cooling the head was submerged by tilting the surgical table head-down, removing the headrest from the table and extending the neck. At the same time the nasal tubes were connected to the outflow tube of pump 1, oral tubes to pump 2, and the scalp tubes to pump 3. Pumps withdrew liquid from the reservoir at 1 L/min for pump 1, at 3 L/min for pump 2 and 5 L/min for pump 3 for a total of 4 L/min through the internally placed catheters and 5 L/min of liquid was directed at the scalp.

The sheep was euthanized after 14 minutes and cooling proceeded for another 22 minutes.

The results of the cooling with propylene glycol are shown in the Table 5. Measurements after death are presented in bold italics.

TABLE 5

Propylene Glycol as Cooling Liquid with
Continued Cooling after Animal Death

| | Temperature (deg C.) | | | | |
|---|---|---|---|---|---|
| Time (min) | Brain | Peri-carotid | Aorta | Bath | Core |
| 0 | 34.6 | 34.7 | 33.9 | −12.9 | 34.2 |
| 1 | 34.6 | 34.7 | 33.9 | −11.6 | 34.2 |

TABLE 5-continued

Propylene Glycol as Cooling Liquid with
Continued Cooling after Animal Death

Temperature (deg C.)

| Time (min) | Brain | Peri-carotid | Aorta | Bath | Core |
|---|---|---|---|---|---|
| 2 | 34.3 | 31.7 | 33.2 | −11.1 | 34.1 |
| 3 | 33.9 | 27.6 | 32.7 | −9.3 | 34 |
| 4 | 33.4 | 25.4 | 32.4 | −7.8 | 33.8 |
| 5 | 33.1 | 24.7 | 32.1 | −5.9 | 33.6 |
| 6 | 32.6 | 25.1 | 31.8 | −3.8 | 33.4 |
| 7 | 32.2 | 22.5 | 31.3 | −2 | 33.2 |
| 8 | 31.8 | 23.1 | 31.3 | 0 | 32.9 |
| 9 | 31.8 | 22.4 | 31.1 | 0 | 32.7 |
| 10 | 31.4 | 21.9 | 31 | 0 | 32.5 |
| 11 | 31.1 | 21.6 | 31 | 1 | 32.3 |
| 12 | 31.1 | 21.6 | 30.9 | 1.4 | 32.3 |
| 13 | 30.8 | 21.4 | 30.8 | 2.3 | 32 |
| 14 | 30.8 | 21.5 | 30 | 2.8 | 31.9 |
| *15* | *30.5* | *21.5* | *31.1* | *3* | *31.9* |
| *16* | *30.5* | *20.4* | *31.2* | *2.5* | *31.9* |
| *17* | *30.5* | *19.4* | *31.2* | *3.5* | *31.9* |
| *18* | *30.2* | *18.7* | *31.3* | *3.3* | *32* |
| *19* | *30.2* | *18.1* | *31.3* | *3* | *32* |
| *20* | *30* | *17.8* | *31.4* | *3* | *32.1* |
| *21* | *30* | *17.3* | *31.4* | *3* | *32.1* |
| *22* | *29.7* | *16.9* | *31.5* | *3.4* | *32.1* |
| *23* | *29.7* | *16.5* | *31.5* | *3* | *32.2* |
| *24* | *29.4* | *16.1* | *31.6* | *3.1* | *32.2* |
| *25* | *29.4* | *15.8* | *31.6* | *3.2* | *32.2* |
| *26* | *29* | *15.4* | *31.5* | *3.5* | *32.3* |
| *28* | *28.7* | *14.8* | *31.6* | *3.8* | *32.4* |
| *32* | *28* | *14.2* | *31.8* | *4.5* | *32.5* |
| *36* | *27.1* | *13.7* | *32.1* | *5.3* | *32.6* |

EXAMPLE 17

Comparison of Aortic Blood Cooling using Nasal vs. Aerodigestive Cooling

Aortic blood temperature data in the following table illustrates the superior rate of systemic blood cooling achieved by introducing the higher flow of liquid into multiple sites along the aerodigestive tract and the scalp. Cooling would be accelerated even more if lower esophageal and stomach catheters were added, and cooling liquid introduced into the aerodigestive tract through them as well. Cooling liquid is also accelerated by using cooling liquid colder than 0° C.

TABLE 6

Aortic Blood Temperature

| time (min) | nasal + oral + upper esophageal + scalp | nasal + scalp |
|---|---|---|
| 0 | 35.5 | 37.7 |
| 1 | 35.6 | 37.6 |
| 2 |  | 37.1 |
| 3 |  | 36.8 |
| 4 | 34.1 | 36.6 |
| 5 | 33.7 | 36.3 |
| 6 | 33.2 | 36.2 |
| 7 | 32.8 | 35.9 |
| 8 | 32.5 | 35.9 |
| 9 | 32.4 | 35.4 |
| 10 | 32.2 | 35.3 |
| 11 | 31.9 | 35.3 |
| 12 | 31.6 | 35.3 |
| 13 | 31.3 | 35.4 |
| 14 | 31.1 | 35.4 |
| 15 | 30.9 | 35.3 |
| 16 | 30.7 | 35.1 |
| 17 |  | 35 |
| 18 |  | 34.5 |
| 19 | 30.5 | 34.5 |
| 20 | 30.4 | 34.7 |
| 21 | 30.2 | 34.7 |
| 22 |  | 34.6 |
| 23 |  | 34.1 |
| 24 |  | 34.1 |
| 25 |  | 34.1 |
| 26 |  | 34.1 |
| 27 |  | 34 |
| 28 |  | 34.1 |
| 29 |  | 34.1 |
| 30 |  | 34.2 |

With regard to Examples 13 to 16, using pure water as the cooling liquid, the addition of esophageal and oral irrigation and turbulent scalp flow to nasal irrigation more than doubled the rate of cerebral temperature drop from 30 min to 13 min for a 5° C. drop in brain temp. A temperature drop of 5° C. in 13 minutes is a remarkable rate of cooling. Head cooling still has an effect even without a pulse. After death of the animal, the core body and aortic temperature actually increased but brain temp continued to decrease. Hence the cooling liquid has a direct effect on the brain, in addition to the effect of cooling blood in the vessels that perfuse the brain.

Brain temperature also decreased significantly in Trial 3 despite two departures from optimal operating conditions. First, the esophageal tube was not optimally placed because the tip remained in the oropharynx in Trial 3 and served as a second oral tube. Second, the high viscosity of the 50% propylene glycol in water cooling liquid resulted in decreased flow rates of liquid into the aerodigestive tract. A much deeper and more rapid temperature drop would be expected with 20% PG and bath temperature of −10° C. because the viscosity would be lower and the flow rates of the liquid in the aerodigestive tract would be greater.

Nonetheless, the blood temperature achieved by adding aerodigestive cooling to scalp cooling is substantially lower than cooling merely the nasal cavity and scalp. Nasal+scalp cooling reached a minimum temperature of only 34° C. and equilibrated, while the addition of aerodigestive cooling achieved a blood temperature of 30° C. and was still decreasing when the experiment ended. This is a substantial difference; without aerodigestive cooling the total temperature drop was 4.7° C., while with aerodigestive cooling the temperature was 3.4° C. cooler in less time and had still not equilibrated.

In Example 16 (Trial 3) with propylene glycol, brain temperature reached a brain temperature of about 28° C. in 32 minutes, even though the experimental subject had been dead for about half that cooling time. Previously published reports have reported reaching temperatures of only about 33.4° C. in 30 minutes. Hence the aerodigestive cooling method is capable to cooling about twice as quickly in the critical first 30 minutes during which therapeutic hypothermia is being initiated.

The addition of esophageal flow helped increase the rate and depth of cooling. There did not appear to be any significant loss of cooling liquid into the stomach from the tube placed in the esophagus. Greater esophageal distension from even higher esophageal flow rates would be expected to increase the surface area of the esophagus, and provide a greater esophageal surface area for heat transfer to occur.

Since the sheep (98 kg) was larger than a typical human adult (60-70 kg), had a skull much thicker than a human skull, and possessed an effective boundary of fur despite close shearing, the rate and depth of direct brain cooling provided by scalp cooling is expected to be greater in humans. However, the inventor has demonstrated a much more rapid rate of cooling is possible using aerodigestive cooling as opposed to nasal cooling alone.

In some embodiments of the method in which more focal hypothermia is desired (for example selective cooling of the brain) the body can be warmed, for example by wrapping the trunk and extremities in heating blankets. The cooling methods disclosed herein cool much more rapidly and deeply than previous methods by cooling a combination of surfaces, and/or using very high rates of flow of cooling liquid. The method is also versatile in that it can be used for substantially specific cooling of the brain alone or less specific cooling of the brain and other organs, either in or remote from a hospital setting or in transit between those sites. The method is capable of deeply cooling about 15% of cardiac blood flow (the blood flow to the head), is non-invasive to the extent that liquid is only introduced into the aerodigestive tract, and can combine internal and external cooling.

All regions cooled are integrated by combining all return liquid from the body, mixing and redelivering liquid to the body. The return of cooling liquid from the body in the experiments was passive, which allows for much higher flow of cooling liquid out of the nose and mouth, and in turn provides more rapid cooling.

The simplicity of the equipment for carrying out the method allows for rapid implementation and broad applicability, so that more people can benefit from the simple sophistication of the approach. The simplicity of design, in which the method can be performed without inserting catheters into organs (such as the brain) leaves vital organs intact and allows more people to benefit from its use. The method and device can be used inside or outside a medical facility so that patients do not have to wait until they reach the emergency room to be treated. The method is suitable for use by less trained medical personnel (such as EMTs) without having to wait for a surgeon to arrive to perform invasive surgical maneuvers (such as introducing cooling catheters into the brain or blood vessels).

The brain can also be maintained significantly colder than the rest of the body during selective cooling, which maximizing brain benefit and minimizes body side effects. Rapid cooling can be induced much faster and attain much lower brain temperatures than with conventional induction of therapeutic hypothermia using prior art methods. In some examples, the temperature in the cerebral cortex is lowered to 33° C. in 5-15 minutes, or 28° C. in 10-20 minutes, or 25° C. in 15-30 minutes. In other examples, the temperature in systemic arterial blood is lowered to 33° C. in 5-15 minutes, to 28° C. in 15-30 minutes, or to 25° C. in 20-40 minutes.

A variety of different catheters/tubes can be used in the devices. Specific, non-limiting examples of particular catheter sizes are given in Example 13. Examples of ranges of catheter sizes are $5/16$ to $½$ inches ID for the scalp tube, $3/16$ to $6/16^{th}$ inches for the esophageal and stomach tubes, $3/16$ to $½$ inches for the mouth tube, and $2/16$ to $6/16^{th}$ inches for the nose tubes.

The method is also capable of rapidly inducing cooling by using "stored cold" for the induction phase in the form of ice water or pre-cooled liquids that are available for emergency use, for example during the first 30 minutes of cooling. The temperature of the cooling liquid is also quite low, and using cooling liquids that are available at sub-zero temperatures to increase the rate and depth of cooling. The volumes of cool liquid available in the reservoir help maintain a sufficient supply for continued high volume flow of cooling liquid.

Organs are cooled by cooling the blood that supplies the organs, so that the disclosed methods do not require total body or even regional cooling to be effective. For example, if cooling of the cervical spinal cord is desired, this low mass region is rapidly cooled without waiting for the much more massive contents of the abdomen to be cooled.

The disclosed methods cool the head, neck and mediastinum using simple but effective techniques to maximize heat transfer. Selective cooling rapidly and deeply cools arterial blood delivered to the brain via the carotid and vertebral arteries. Non-selective cooling is capable of cooling venous blood returning to the heart, and therefore the systemic arterial blood. The venous blood is cooled in two regions, the neck and the mediastinum. The temperature of the blood draining from the neck is very low, in time approaching the temperature of the cold liquid bath that bathes it. This is due to cooling of the blood in the head and neck at the capillary level (most profound in the tissue beds in proximity to the skin and mucus membranes that are in direct contact with the cooling fluid) in addition to cooling of the blood in the jugular veins via cold fluid in the upper airway. About 15% of the cardiac output will be cooled in this very efficient manner.

The esophagus traverses the entire mediastinum and is in close proximity to the inferior vena cava, superior vena cava and the heart. The vena cava carries the entire cardiac output back to the heart. It is thin walled and lies in very close proximity to the esophagus, allowing for very efficient heat transfer with the esophagus. The stomach is in close proximity to the inferior vena cava as well as the inferior surface of the heart.

Direct contact of cooling liquids with the aerodigestive tract (as opposed to placing the liquid in a container within the tract) allows for the full surface area of the aerodigestive tract (from nares to pylorus) to be used for heat exchange. The cooling liquid enters irregular areas of the surface that balloons or rigid devices would not reach. Examples of such irregular surfaces that are bathed with the cooling liquid are the nasal trabeculae, tonsils, and larynx.

In addition to the high flow of cool liquid through the aerodigestive tract, turbulent flow of the cooling liquid (both externally against the face and scalp and internally in the aerodigestive tract) contributes to heat exchange. For example, a thick layer of stagnant liquid at the outer aspects of the esophageal lumen could cause the flow of cool liquid to flow down only a central core that reduces heat exchange. Turbulence of flow is increased by having multiple points of liquid delivery (multiple catheters and each catheter can have side holes), high flow rates, crossed currents of liquid flow (liquid is pushed into the body and generally directed towards the feet but changes direction and is expelled out the mouth and nose), encountering irregular surfaces in the aerodigestive tract (not smoothed over by a bag or balloon) and the presence of multiple delivery tubes along the path of liquid exit.

Another advantage of the method is that it is capable of providing the internal delivery of the cool liquid to the aerodigestive tract without immersing other parts of the body (such as the chest, extremeties or even in the head in some embodiments) in cooling liquid. Hence it is possible to perform other interventions on the patient that would not be possible in other types of induced hypothermia. Examples of such interventions include electrical cardioversion (applying electrical energy to the heart to change or initiate its rhythm), electrocardiography (obtaining diagnostic signals from the heart by applying external electrodes to the body, including the thorax), or performing cardiac or neurovascular surgery (such as angioplasty or stenting).

Although the methods and devices have been described in association with certain theories of their operation, the invention is not to be limited by those theories. To the extent that the invention can be understood in terms of the described structures and methods, the claims do not incorporate theories of operation unless the claims clearly indicate otherwise.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A method for selective and non-invasive cooling of the brain comprising:
   positioning a plurality of catheters into a patient;
   directing an amount of free flowing non-nebulized fluid into the oropharynx, hypopharynx, and esophagus of the patient through the plurality of catheters; and
   replenishing free flowing non-nebulized fluid that is discharged from the patient by introducing an additional amount of free flowing non-nebulized fluid into the oropharynx, hypopharynx, and esophagus of the patient.

2. The method of claim 1, wherein the free flowing non-nebulized fluid is also directed into the nasopharynx of the patient.

3. The method of claim 1, wherein the discharge of free flowing nonnebulized fluid is performed by suctioning the free flowing non-nebulized fluid from the patient.

4. The method of claim 1, further comprising externally cooling the scalp of the patient.

5. The method of claim 1, wherein the plurality of catheters comprises at least one catheter that extends into the esophagus to direct fluid into the esophagus.

6. The method of claim 1, wherein the plurality of catheters comprises at least one catheter that extends through the oral cavity of the patient.

7. The method of claim 1, wherein the plurality of catheters comprises at least one catheter that extends through the oral cavity and at least one catheter that extends through the nasal cavity of the patient.

8. The method of claim 1, further comprising restricting flow of the free flowing non-nebulized fluid to the trachea by positioning an endotracheal tube with a distal cuff in the trachea.

9. The method. of claim 1, further removing fluid from within the patient through one or more ports within the endotracheal tube.

10. The method of claim 1, wherein the temperature of the free flowing nonnebulized fluid is less than about 32 degrees Celsius when entering the patient.

11. The method of claim 1, wherein the temperature of the free flowing nonnebulized fluid is between about 0 and 32 degrees Celsius when entering the patient.

12. An apparatus for selective and non-invasive cooling of the brain comprising:
   a first nasal catheter sized to be received through a first nostril of a patient, the first nasal catheter having a length selected so that a proximal end extends out of the first nostril of the patient and a distal end of the first nasal catheter is located in the vicinity of the nasopharynx of the patient when the first nasal catheter is received through the first nostril;
   a pair of esophageal catheters comprising a first esophageal catheter and a second esophageal catheter, each of the pair of esophageal catheters being sized to be inserted into the esophagus of the patient and having a length that extends past the hypopharynx of the patient, wherein the first esophageal catheter terminates with a cuff that restricts the flow of fluid past the cuff and the second esophageal catheter has a distal end that terminates within the esophagus proximal to the cuff; and
   a pair of tracheal catheters comprising a first tracheal catheter and a second tracheal catheter, each of the pair of tracheal catheters being sized to be inserted into the trachea of the patient, wherein the first tracheal catheter terminates with a cuff that restricts the flow of fluid past the cuff and the second tracheal catheter has a distal end that terminates distal to the cuff to allow the passage of air into and out of the lungs of the patient.

13. The apparatus of claim 12, further comprising a second nasal catheter configured to be received through the first nostril or a second nostril of the patient.

14. The apparatus of claim 12, wherein the pair of esophageal catheters are coupled to one another to form a single multi-lumen esophageal catheter.

15. The apparatus of claim 12, wherein the pair of tracheal catheters are coupled to one another to form a single multi-lumen tracheal catheter.

16. The apparatus of claim 12, further comprising a third tracheal catheter with a proximal end that extends outside of the patient and a distal end that terminates proximal to the cuff.

17. The apparatus of claim 16, wherein the first, second, and third tracheal catheters are coupled together to form a single multi-lumen tracheal catheter.

18. The apparatus of claim 12, further comprising an oral catheter configured to have a proximal end that extends out of the patient and a distal end that terminates in the vicinity of the oropharynx and/or hypopharynx.

19. The apparatus of claim 12, further comprising a container for receiving at least a portion of the head of the patient.

20. The apparatus of claim 12, further comprising at one drainage tube sized to be received within the oral cavity to withdraw fluid from the oral cavity.

21. The apparatus of claim 12, wherein the distal end of the second esophageal catheter does not extend within the esophagus to a position that is distal to the vicinity of the aortic arch of the patient.

22. The apparatus of claim 16, wherein the third tracheal catheter comprises a suction port proximal to the cuff of the first tracheal catheter.

23. A method for selective and non-invasive cooling of the brain, the method comprising:
   delivering free flowing fluid into the aerodigestive tract of a patient at a first location in the aerodigestive tract, the first location being within an upper aerodigestive tract of the patient; and
   concurrently delivering free flowing fluid into the aerodigestive tract of the patient at a second location in the aerodigestive tract, the second location being within a portion of the aerodigestive tract that does not include the upper aerodigestive tract.

24. The method of claim 23, wherein the free flowing fluid is a non-nebulized fluid.

25. The method of claim 24, wherein the first location is in the upper airway of the patient.

26. The method of claim 24, wherein the second location is in the esophagus of the patient.

27. The method of claim 24, wherein the second location is proximal to the vicinity of the aortic arch of the patient.

* * * * *

UNITED STATES PATENT AND TRADEMARK OFFICE
CERTIFICATE OF CORRECTION

| | | |
|---|---|---|
| PATENT NO. | : 8,308,787 B2 | Page 1 of 1 |
| APPLICATION NO. | : 12/842860 | |
| DATED | : November 13, 2012 | |
| INVENTOR(S) | : Thomas Kreck | |

It is certified that error appears in the above-identified patent and that said Letters Patent is hereby corrected as shown below:

In claim 20, column 48, line 35, delete "at one" and insert --at least one-- therefor.

Signed and Sealed this
Eighteenth Day of December, 2012

David J. Kappos
*Director of the United States Patent and Trademark Office*